United States Patent
Ardehali et al.

(10) Patent No.: US 10,258,612 B2
(45) Date of Patent: Apr. 16, 2019

(54) MITOCHONDRIAL LIPID PERMEABLE IRON CHELATORS FOR TREATING AND PREVENTING ISCHEMIA/REPERFUSION (I/R) INJURY IN THE HEART FOLLOWING AN ISCHEMIC EVENT

(71) Applicant: Northwestern University, Evanston, IL (US)

(72) Inventors: Hossein Ardehali, Hinsdale, IL (US); Hsiang-Chun Chang, Chicago, IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 15/209,261

(22) Filed: Jul. 13, 2016

(65) Prior Publication Data

US 2017/0014397 A1    Jan. 19, 2017

Related U.S. Application Data

(60) Provisional application No. 62/192,242, filed on Jul. 14, 2015.

(51) Int. Cl.
  *A61K 31/16*    (2006.01)
  *A61K 31/444*   (2006.01)

(52) U.S. Cl.
  CPC ............ *A61K 31/444* (2013.01); *A61K 31/16* (2013.01)

(58) Field of Classification Search
  CPC .............................. A61K 31/16; A61K 31/444
  See application file for complete search history.

(56) References Cited

U.S. PATENT DOCUMENTS

2006/0293292 A1* 12/2006 Cardozo .............. A61K 31/166
                                                                    514/169

OTHER PUBLICATIONS

Chang et al. (Circulation, Nov. 25, 2014, vol. 130, Issue Suppl 2).*
Liang et al. (The J of Neuroscience, 2008, 28(45):11550-11556).*
Wren Copyright ©2017 Diabetes Self-Management.*
Wu et al. (Neurobio Dis. Jan. 2012; 45(1): 388-394).*
Hruskova et al. (Chem. Res. Toxicol. 2011, 24, 290-302).*
Horackova. (Cardiovascular Research 47 (2000) 529-536).*
Kovacevic et al. (Chem. Res. Toxicol. 2011, 24, 2279-282).*
Abbate et al., "Dual selective iron chelating probes with a potential to monitor mitochondrial labile iron," Chem. Commun. 2016, 52, 784-787.
Alta et al., "Mitochondria-penetrating peptides conjugated to desferrioxamine as chelators for mitochondrial labile iron," PLoS One, Feb. 8, 2017.
Cloonan et al., "Mitochondrial iron chelation ameliorates cigarette smoke-induced bronchitis and emphysema in mice," Nat. Med. 22, 163-174 (2016).
Kalinowski et al., "The Evolution of Iron Chelators for the Treatment of Iron Overload Disease and Cancer," Pharma. Rev. 57:547-583, 2005.
Mena et al., "The novel mitochondrial iron chelator 5-((methylamino)methyl)-8-hydroxyquinoline protects against mitochondrial-induced oxidative damage and neuronal death," Biochem. Biophys. Res. Commun. Aug. 2015. 7;463 (4):787-92.
Reelfs et al., "A Powerful Mitochondria-Targeted Iron Chelator Affords High Photoprotection against Solar Ultraviolet A Radiation," J. Invest. Derma. (2016) 136, 1692-1700.
Richardson DR, "Friedreich's ataxia: iron chelators that target the mitochondrion as a therapeutic strategy?" Expert Opin. Invest. Drugs, vol. 12, 2003—Issue 2, published online Mar. 2, 2005.
Adlam et al., "Targeting an Antioxidant to Mitochondria Decreases Cardiac Ischemia-Reperfusion Injury", FASEB Journal : Official Publibcation of the Federation of American Societies for Experimental Biology, 2005, 19:1088-1095.
Aigner et al., "Pathways Underlying Iron Accumulation in Human Nonalcoholic Fatty Liver Disease", The American Journal of Clinical Nutrition, 2008, 87:1374-1383.
Anker et al., "Ferric Carboxymaltose in Patients with Heart Failure and Iron Deficiency", New England Journal of Medicine, 2009, 361:2436-2448.
Ardehali et al., "Cardioprotective Role of the Mitochondrial ATP-Binding Cassette Protein 1", Circulation Research, 2005, 97:740-742.
Badylak et al., "Protection from reperfusion injury in the isolated rat heart by postischaemic deferoxamine and oxypurinol administration", Cardiovascular Research, 1987, 21:500-506.
Braunwald et al., "Heart Failure", JACC: Heart Failure, 2013, 1:1-20.
Brazzolotto et al., "Human Cytoplasmic Aconitase (Iron Regulatory Protein 1) Is Converted into Its [3Fe-4S] Form by Hydrogen Peroxide in Vitro but Is Not Activated for Iron-responsive Element Binding", Journal of Biological Chemistry, 1999, 274:21625-21630.
Cabantchik et al., "A fluorescence assay for assessing chelation of intracellular iron in a membrane model system and in mammalian cells", Analytical biochemistry, 1996, 233:221-227.
Cantu et al., "Oxidative Inactivation of Mitochondrial Aconitase Results in Iron and H2O2-Mediated Neurotoxicity in Rat Primary Mesencephalic Cultures", PLoS ONE, 2009, 4:e7095.
Chan et al., "Effect of Iron Chelation on Myocardial Infarct Size and Oxidative Stress in ST-Elevation.Myocardial Infarction", Circulation: Cardiovascular Interventions, 2012, 5:270-278.
Chatziathanasiou et al., "Combined intravenous treatment with ascorbic acid and desferrioxamine to reduce myocardial reperfusion injury in an experimental model resembling the clinical setting of primary PCI", Hellenic Journal of Cardiology, 2012, 2012:195-204.
Chen et al., "Cardiac mitochondria and reactive oxygen species generation", Circ Res, 2014, 114:524-537.
Chopra et al., "Decrease of myocardial infarct size with desferrioxamine: possible role of oxygen free radicals in its ameliorative effect", Molecular and Cellular Biochemistry, 1992, 113:71-76.
Comporti et al., "Iron release, oxidative stress and erythrocyte ageing", Free radical biology & medicine, 2002, 32:568-576.

(Continued)

*Primary Examiner* — Shirley V Gembeh
(74) *Attorney, Agent, or Firm* — Andrus Intellectual Property Law, LLP

(57) ABSTRACT

Disclosed are methods and compositions for treating or preventing a disease or disorder responsive to a decrease in baseline mitochondrial iron in a subject in need thereof. The methods typically include administering a pharmaceutical composition comprising a mitochondrial permeable iron chelator to the subject.

4 Claims, 19 Drawing Sheets

(56) References Cited

OTHER PUBLICATIONS

Coudray et al., "Effect of ischemia/reperfusion sequence on cytosolic iron status and its release in the coronary effluent in isolated rat hearts", Biol Trace Elem Res, 1194, 41:69-75.
Dai et al., "Mitochondrial targeted antioxidant Peptide ameliorates hypertensive cardiomyopathy", J Am Coll Cardiol, 2011, 58:73-82.
Davidson et al., "Effects of NO on mitochondrial function in cardiomyocytes: Pathophysiological relevance", Cardiovascular Research, 2006, 71:10-21.
De Domenico et al., "Regulation of iron acquisition and storage: consequences for iron-linked disorders", Nat Rev Mol Cell Biol, 2008, 9:72-81.
De Vries et al., "Reduction of circulating redox-active iron by apotransferrin protects against renal ischemia-reperfusion injury", Transplantation, 2004, 77: 669-675.
Demougeot et al., "Cytoprotective Efficacy and Mechanisms of the Liposoluble Iron Chelator 2,2'-Dipyridyl in the Rat Photothrombotic Ischemic Stroke Model", Journal of Pharmacology and Experimental Therapeutics, 2004, 311:1080-1087.
Dixon et al., "The role of iron and reactive oxygen species in cell death", Nat Chem Biol, 2014, 10:9-17.
Doulias et al., "Endosomal and lysosomal effects of desferrioxamine: protection of HeLa cells from hydrogen peroxide-induced DNA damage and induction of cell-cycle arrest", Free Radical Biology and Medicine, 2003, 35:719-728.
Eaton et al., "Molecular bases of cellular iron toxicity", Free Radical Biology and Medicine, 2002, 32: 833-840.
Flint et al., "The inactivation of Fe—S cluster containing hydro-lyases by superoxide", Journal of Biological Chemistry, 1993, 268:22369-22376.
Foo Rsy et al., "Death begets failure in the heart", The Journal of Clinical Investigation, 2005, 115: 565-571.
Fortmann et al., "Vitamin and mineral supplements in the primary prevention of cardiovascular disease and cancer: An updated systematic evidence review for the U.S. Preventive Services Task Force", Ann Intern Med, 2013, 159:824-834.
Frank et al., "The Role of Dynamin-Related Protein 1, a Mediator of Mitochondrial Fission, in Apoptosis", Developmental Cell, 2001, 1:515-525.
Furukawa et al., "Iron deprivation decreases ribonucleotide reductase activity and DNA synthesis", Life sciences, 1992, 50:2059-2065.
Gane et al., "The mitochondria-targeted anti-oxidant mitoquinone decreases liver damage in a phase II study of hepatitis C patients", Liver international : official journal of the International Association for the Study of the Liver, 2010, 30:1019-1026.
Gao et al., "Mitochondrial DNA Damage in Iron Overload", Journal of Biological Chemistry, 2009, 284:4767-4775.
Ghio et al., "Disruption of iron homeostasis and lung disease", Biochimica et Biophysica Acta (BBA)—General Subjects, 2009, 1790:731-739.
Gille et al., "Iron-dependent functions of mitochondria.relation to neurodegeneration", J Neural Transm, 2011, 118:349-359.
Gomez et al., "Malfunctioning of the Iron-Sulfur Cluster Assembly Machinery in *Saccharomyces cerevisiae* Produces Oxidative Stress via an Iron-Dependent Mechanism, Causing Dysfunction in Respiratory Complexes", PLoS ONE, 2014, 9:e111585.
Hentze et al., "Two to Tango: Regulation of Mammalian Iron Metabolism", Cell, 2010, 142:24-38.
Heron (2013) Deaths: Leading Causes for 2010. In National Vital Statistics Report. Hyattsville, MD: National Center for Health Statistics.
Hirst, "Mitochondrial Complex I", Annual Review of Biochemistry, 2013, 82:551-575.
Hollenbeck et al., "Early cardiac catheterization is associated with improved survival in comatose survivors of cardiac arrest without STEMI", Resuscitation, 2014, 85:88-95.
Horowitz et al., "Mitochondrial iron metabolism and its role in neurodegeneration", Journal of Alzheimer's disease: JAD 20 Suppl, 2010, 2:S551-568.

Ichikawa et al., "Disruption of ATP-binding cassette B8 in mice leads to cardiomyopathy through a decrease in mitochondrial iron export", Proceedings of the National Academy of Sciences, 2014, 109:4152-4157.
Ichikawa et al., "Cardiotoxicity of doxorubicin is mediated through mitochondrial iron accumulation", The Journal of Clinical Investigation, 2014, 124:617-630.
Jang et al., "Micromolar Intracellular Hydrogen Peroxide Disrupts Metabolism by Damaging Iron-Sulfur Enzymes", Journal of Biological Chemistry, 2007, 282:929-937.
Jha et al., "The Antioxidant Vitamins and Cardiovascular Disease: A Critical Review of Epidemiologic and Clinical Trial Data", Annals of Internal Medicine, 1995, 123: 860-872.
Jheng et al., "Mitochondrial Fission Contributes to Mitochondrial Dysfunction and Insulin Resistance in Skeletal Muscle", Molecular and Cellular Biology, 2012, 32:309-319.
Kaushal et al., "Challenges and Advances in the Treatment of AKI", Journal of the American Society of Nephrology, 2014, 25:877-883.
Khechaduri et al., "Heme Levels Are Increased in Human Failing Hearts", Journal of the American College of Cardiology, 2013, 61:1884-1893.
Kispal et al., "Biogenesis of cytosolic ribosomes requires the essential iron-sulphur protein Rli1p and mitochondria", EMBO J, 2005, 24:589-598.
Kobayashi et al., "Coronary venous retroinfusion of deferoxamine reduces infarct size in pigs", Journal of the American College of Cardiology, 1991, 18:621-627.
Kurz T et al., (2010) Redox activity within the lysosomal compartment: implications for aging and apoptosis. Antioxidants & redox signaling 13: 511-523.
Lamas et al. "Effect of disodium edta chelation regimen on cardiovascular events in patients with previous myocardial infarction: The tact randomized trial", JAMA, 2013, 309: 1241-1250.
Lesnefsky et al. "High-Dose Iron-Chelator Therapy During Reperfusion with Deferoxamine-Hydroxyethyl Starch Conjugate Fails to Reduce Canine Infarct Size", Journal of Cardiovascular Pharmacology, 1990, 16:523-528.
Lesnefsky et al. "Schemia-reperfusion injury in the aged heart: role of mitochondria", Archives of biochemistry and biophysics, 2003, 420:287-297.
Lesnefsky et al. "Deferoxamine pretreatment reduces canine infarct size and oxidative injury", Journal of Pharmacology and Experimental Therapeutics, 1990, 253:1103-1109.
Li et al. "Expression of the yeast cation diffusion facilitators Mmt1 and Mmt2 affects mitochondrial and cellular iron homeostasis: evidence for mitochondrial iron export", The Journal of biological chemistry, 2014, 289:17132-17141.
Liang et al. "Increasing Post-Myocardial Infarction Heart Failure Incidence in Elderly Patients: A Call for Action", Journal of the American College of Cardiology, 2009, 53:21-23.
Lloyd et al. "Evidence that desferrioxamine cannot enter cells by passive diffusion", Biochemical pharmacology, 1991 41:1361-1363.
Long et al. "Mitochondrial Ca2+ flux and respiratory enzyme activity decline are early events in cardiomyocyte response to H2O2", J Mol Cell Cardiol, 2004 37:63-70.
Marcus et al. "Desferrioxamine to improve cardiac function in iron-overloaded patients with thalassemia major", Lancet (London, England), 1984, 1:392-393.
McAlindon et al. "Infarct size reduction in acute myocardial infarction", Heart, 2015, 101:155-160.
Menasche et al. "Iron chelation by deferoxamine inhibits lipid peroxidation during cardiopulmonary bypass in humans", Circulation, 1990, 82:IV390-396.
Methy et al. "Beneficial effect of dipyridyl, a liposoluble iron chelator against focal cerebral ischemia: In vivo and in vitro evidence of protection of cerebral endothelial cells", Brain Research, 2008, 1193:136-142.
Moser et al. "Inhibition of succinate-linked respiration and complex II activity by hydrogen peroxide", Archives of biochemistry and biophysics, 2009, 488:69-75.
Murphy "How mitochondria produce reactive oxygen species", The Biochemical journal, 2009, 417:1-13.

(56) References Cited

OTHER PUBLICATIONS

Napier et al. "Iron trafficking in the mitochondrion: novel pathways revealed by disease", Blood, 2005, 105:1867-1874.

Neuzil et al. "Mitochondria transmit apoptosis signalling in cardiomyocyte-like cells and isolated hearts exposed to experimental ischemia-reperfusion injury", Redox report : communications in free radical research, 2007, 12:148-162.

Nichols et al. "European Cardiovascular Disease Statistics, 2012 Edition: European Heart Network, Brussels, European Society of Cardiology, Sophia Antipolis".

Nicholson et al. "Effect of Desferrioxamine Cardioplegia on Ischemia-Reperfusion Injury in Isolated Rat Heart", The Annals of thoracic surgery, 1997, 63:1003-1011.

Paraskevaidis et al. "Deferoxamine infusion during coronary artery bypass grafting ameliorates lipid peroxidation and protects the myocardium against reperfusion injury: immediate and long-term significance", European heart journal, 2005, 26:263-270.

Pepe et al. "Deferasirox, deferiprone and desferrioxamine treatment in thalassemia major patients: cardiac iron and function comparison determined by quantitative magnetic resonance imaging", Haematologica, 2011, 96:41-47.

Persson et al. "Radiation-induced cell death: importance of lysosomal destabilization", Biochemical Journal, 2005, 389:877-884.

Petrat et al. "The Chelatable Iron Pool in Living Cells: A Methodically Defined Quantity", Biological Chemistry, 2002, 383:489-502.

Petrat et al. "Selective determination of mitochondrial chelatable iron in viable cells with a new fluorescent sensor", The Biochemical journal, 2002, 362:137-147.

Pletjushkina et al. "Effect of oxidative stress on dynamics of mitochondrial reticulum", Biochimica et Biophysica Acta (BBA)—Bioenergetics, 2006, 1757:518-524.

Ponikowski et al. "Beneficial effects of long-term intravenous iron therapy with ferric carboxymaltose in patients with symptomatic heart failure and iron deficiency", European Heart Journal, 2014, 36:657-668.

Porter et al. "Treatment of heart failure in adults with thalassemia major: response in patients randomised to deferoxamine with or without deferiprone", Journal of Cardiovascular Magnetic Resonance, 2013, 15:38.

Ramesh et al. "Early treatment with deferoxamine limits myocardial ischemic/reperfusion injury", Free Radical Biology and Medicine, 1989, 7:45-52.

Rauen et al. "Assessment of Chelatable Mitochondrial Iron by Using Mitochondrion-Selective Fluorescent Iron Indicators with Different Iron-Binding Affinities", ChemBioChem, 2007, 8:341-352.

Roy et al. "Transcriptome analysis of the ischemia-reperfused remodeling myocardium: temporal changes in inflammation and extracellular matrix", Physiological genomics, 2006, 25:364-374.

Schieber et al. "ROS function in redox signaling and oxidative stress", Current biology : CB, 2014, 24:R453-462.

Shakoury-Elizeh et al. "Metabolic Response to Iron Deficiency in *Saccharomyces cerevisiae*", Journal of Biological Chemistry, 2010, 285:14823-14833.

Sideri et al. "Methionine sulphoxide reductases protect iron.sulphur clusters from oxidative inactivation in yeast", Microbiology, 2009, 155:612-623.

Simoons et al. "Early thrombolysis in acute myocardial infarction: limitation of infarct size and improved survival", J Am Coll Cardiol, 1986, 7:717-728.

Spinazzi et al. "Assessment of mitochondrial respiratory chain enzymatic activities on tissues and cultured cells", Nature protocols, 2012, 7:1235-1246.

Steinhubl et al. "Why Have Antioxidants Failed in Clinical Trials", The American journal of cardiology, 2008, 101: S14-S19.

Tang et al. "Polyol pathway mediates iron-induced oxidative injury in ischemic reperfused rat heart", Free Radical Biology and Medicine, 2008, 45:602-610.

Vasquez-Vivar et al. "Mitochondrial Aconitase Is a Source of Hydroxyl Radical: an electron spin resonance investigation", Journal of Biological Chemistry, 2000, 275:14064-14069.

Verhaar et al. "Free radical production by dysfunctional eNOS", Heart, 2004, 90:494-495.

Vigani et al. "Mitochondrial ferritin is a functional iron-storage protein in cucumber (*Cucumis sativus*) roots", Frontiers in plant science, 2013, 4:316.

Watanabe et al. "Failure of Deferoxamine to Reduce Myocardial Infarct Size in a Primate Model of Ischemia-Reperfusion Injury", Journal of Surgical Research, 1993, 55:537-542.

Williams et al. "Treatment with deferoxamine during ischemia improves functional and metabolic recovery and reduces reperfusion-induced oxygen radical generation in rabbit hearts", Circulation, 1991, 83:1006-1014.

Wu et al. "Efficacy of the lipid-soluble iron chelator 2,2 (E-dipyridyl against hemorrhagic brain injury", Neurobiology of Disease, 2012, 45:388-394.

Wu et al. "Glutaredoxin 2 prevents H2O2-induced cell apoptosis by protecting complex I activity in the mitochondria", Biochimica et Biophysica Acta (BBA)—Bioenergetics, 2010, 1797:1705-1715.

Wu et al. "Reduction in Hexokinase II Levels Results in Decreased Cardiac Function and Altered Remodeling After Ischemia/Reperfusion Injury", Circulation Research, 2011, 108:60-69.

Xu et al. "Formation of hydrogen peroxide and reduction of peroxynitrite via dismutation of superoxide at reperfusion enhances myocardial blood flow and oxygen consumption in postischemic mouse heart", The Journal of pharmacology and experimental therapeutics, 2008, 327:402-410.

Ye et al. "Human Iron-Sulfur Cluster Assembly, Cellular Iron Homeostasis, and Disease", Biochemistry, 2010, 49: 4945-4956.

Yu et al. "Intralysosomal iron: a major determinant of oxidant-induced cell death", Free Radical Biology and Medicine, 2003, 34:1243-1252.

Zhang et al. "Translocation of iron from lysosomes to mitochondria during ischemia predisposes to injury after reperfusion in rat hepatocytes", Free radical biology & medicine, 2013, 63:243-253.

Zhao et al. "Role of iron in ischemia-reperfusion oxidative injury of rat lungs", American Journal of Respiratory Cell and Molecular Biology, 1997, 16:293-299.

Zweier et al. "The role of oxidants and free radicals in reperfusion injury", Cardiovascular Research, 2006, 70:181-190.

* cited by examiner

Figure 10
A
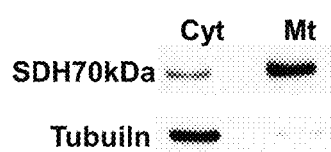
B
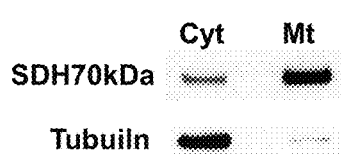
C
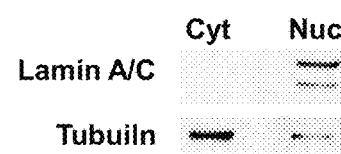

MITOCHONDRIAL LIPID PERMEABLE IRON CHELATORS FOR TREATING AND PREVENTING ISCHEMIA/REPERFUSION (I/R) INJURY IN THE HEART FOLLOWING AN ISCHEMIC EVENT

CROSS-REFERENCE TO RELATED PATENT APPLICATIONS

This application claims the benefit of priority under 35 U.S.C. § 119(e) to U.S. Provisional Application No. 62/192,242, filed on Jul. 14, 2015, the content of which is incorporated herein by reference in its entirety.

STATEMENT REGARDING FEDERALLY SPONSORED RESEARCH OR DEVELOPMENT

This invention was made with government support under grant number R01 H1087149 awarded by the National Institutes of Health. The government has certain rights in the invention.

BACKGROUND

The field of the invention relates to methods for treating and/or preventing cell death and organ damage in a subject following an ischemic event. In particular, the field of the invention relates to methods for treating and/or preventing cell death and organ damage in a subject following an ischemic event by administering an iron chelator to the subject.

Heart failure is a common disorder and our current treatments are limited. In the past few years, several studies have suggested that giving iron supplementation may be beneficial in certain patients with iron deficiency and heart failure. However, these studies have only shown an improvement in symptoms in patients with heart failure and studies on the improvement of cardiac function in these patients is limited. Furthermore, earlier studies had indicated that an increase in mitochondrial iron in the heart is associated with cardiomyopathy. Iron is an essential molecule for normal cellular physiology. However, in excess iron is also a source of oxidative stress and cellular damage. Other studies had shown that iron chelators, which function by chelating and reducing cellular iron, reduce cardiac damage only in some cases, and some studies had shown no benefit of treatment with these molecules. Based on these prior art, the present inventors hypothesized that a reduction in mitochondrial iron would be protective against the development of heart failure. Here, the inventors show in tissue culture and in animal models that a reduction in mitochondrial iron is protective against ischemic injury in the heart and the development of cardiomyopathy.

SUMMARY

Disclosed are methods and compositions for treating or preventing a disease or disorder responsive to a decrease in baseline mitochondrial iron in a subject in need thereof. The methods typically include administering a pharmaceutical composition comprising a mitochondrial permeable iron chelator to the subject.

When practiced, the disclosed methods preferably protect against cell death and organ damage in the subject after an ischemic event. In some embodiments, the subject has experienced or is at risk for developing cardiomyopathy, heart failure, or ischemic heart disease, and preferably the method protects against ischemia/reperfusion (I/R) injury in the heart. In other embodiments, the subject has experienced or is at risk for experiencing a stroke, and preferably the method protects against ischemia in the brain.

In the disclosed methods, the administered iron chelator is permeable to the mitochondria of target cells (e.g., cardiomyocytes, neurons, and the like). The administered iron chelator preferably is lipophilic. Suitable mitochondrial permeable iron chelators may include, but are not limited to chelators selected from the group consisting of di-pyridyl compounds, siderophores, ICL670A, deferiprone and hydroxypyridinone analogs, tachpyridine, aryoylhydrazones, and thiosemicarbazones.

BRIEF DESCRIPTION OF THE FIGURES

FIG. 10. Representative Western Blots from subcellular fractions. A. Presence of cytosolic marker (tubulin) and mitochondrial marker (SDH70 kDa) in respective subcellular fractions from mouse heart. Equal amounts of protein from each fraction were loaded onto the gel. Cyt=cytosolic fraction. Mt=mitochondrial fraction. B. Presence of cytosolic marker (tubulin) and mitochondrial marker (SDH70 kDa) in respective subcellular fractions from human heart. Equal amounts of protein from each fraction were loaded onto the gel. C. Presence of cytosolic marker (tubulin) and nuclear marker (Lamin A/C) in respective subcellular fractions from mouse heart. Cyt=cytosolic fraction. Nuc=nuclear fraction.

DETAILED DESCRIPTION

Figure 1:
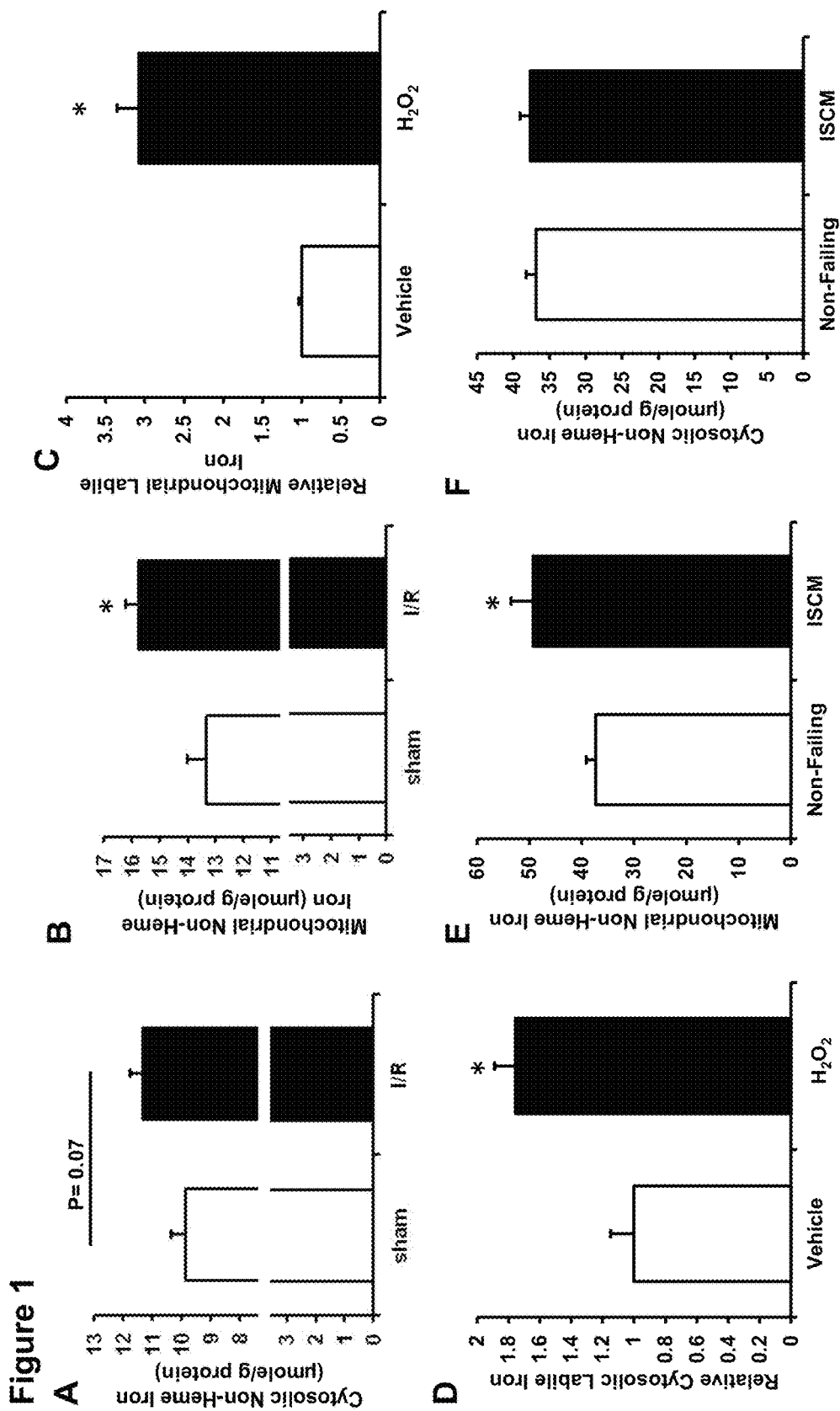
FIG. 1. Ischemia/reperfusion (I/R) injury in vivo causes increased mitochondrial iron. A. Cytosolic non-heme iron levels in wild-type mice subjected to sham or I/R procedure two days after surgery. N=4-5 for each group. B. Mitochondrial non-heme iron levels in wild-type mice subjected to sham or I/R procedure two days after surgery. * P<0.05. N=4-5 for each group. C. Mitochondrial labile iron in H9c2 cells with or without $H_2O_2$ treatment measured using RPA fluorescence. * P<0.05. N=8-12 for each group. D. Cytosolic labile iron in H9c2 cells with or without $H_2O_2$ treatment measured using calcein fluorescence. * P<0.05. N=4-6 in each group. E. Mitochondrial iron in human cardiac tissue sample from non-failing hearts and from hearts with ischemic cardiomyopathy (ISCM). * P<0.05. N=4 in each group. F. Cytosolic iron in human cardiac tissue sample from non-failing hearts and from hearts with ischemic cardiomyopathy (ISCM). N=4 in each group.

Disclosed are methods and compositions for treating or preventing a disease or disorder responsive to a decrease in baseline mitochondrial iron in a subject in need thereof. The methods and compositions may be described based on the following definitions.

Unless otherwise specified or indicated by context, the terms "a", "an", and "the" mean "one or more." In addition, singular nouns such as "chelator" should be interpreted to mean "one or chelators."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The terms "subject," "patient," or "host" may be used interchangeably herein and may refer to human or non-human animals. Non-human animals may include, but are not limited to non-human primates, dogs, and cats.

The terms "subject," "patient," or "individual" may be used to a human or non-human animal having or at risk for experiencing a disease or disorder that is responsive to a decrease in baseline mitochondrial iron. Subjects that may be treated by the disclosed methods and compositions may include subjects having or at risk for developing a disease or disorder characterized by an ischemic event where the disclosed methods protects against cell death and organ damage in the subject following the ischemic event. Suitable subjects may include subjects that have experienced or are at risk for developing cardiomyopathy, heart failure, or ischemic heart disease, where the disclosed treatment method protects against ischemia/reperfusion (I/R) injury in the heart. Suitable subject may include subjects that experienced or are risk for experiencing a stroke, where the treatment method protects against ischemia in the brain.

A "subject in need thereof" may include a subject having, for example, a cardiac disease or condition and/or atherosclerosis. A "subject in need thereof" may include a subject undergoing therapy to treat a disease or condition that may include, but is not limited to, a cardiac disease or condition and/or atherosclerosis. As used herein, "cardiac diseases or conditions" may include structural heart diseases (e.g., myocardial infarction, cardiac dysfunction following myocardial infarction, reduced myocardial contractility, end-stage valve disease, and dilated cardiomyopathy). Cardiac diseases or conditions may include those diseases or conditions associated with ischemic injury, which means the damage or potential damage to an organ or tissue that results from the interruption of blood flow to the organ or tissue (i.e., an "ischemic event"). A "subject in need thereof" can be a subject diagnosed as having a myocardial infarction. The subject can be a subject diagnosed as having post-infarction cardiac dysfunction. The subject can be a subject who has been diagnosed as having had a myocardial infarction who is, thus, at increased risk of developing post-infarction cardiac dysfunction. Furthermore, the subject can be a subject diagnosed as having dilated cardiomyopathy or symptoms of heart failure from any cause associated with a phenotype of cardiac chamber dilation and reduced myocardial contractile function. The subject can be a subject diagnosed as having reduced myocardial contractility. The subject can be a subject diagnosed with atrial fibrillation.

A "subject in need thereof" may include a subject having, for example, a proliferative disease or disorder such as cancers or hyperproliferative disorders that are associated with increased mitochondrial iron, which may include, but are not limited to adenocarcinoma, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

A "subject in need thereof" may include a subject having, for example, a neurodegenerative disease or disorder that is associated with increased mitochondrial iron. Neurodegenerative diseases or disorders may include, but are not limited to amyotrophic lateral sclerosis, Parkinson's disease, Alzheimer's disease, and Huntington's disease.

The methods disclosed herein may have a variety of applications. These include, but are not limited to treatment of heart failure, protection against Ischemia/Reperfusion damage in the heart, treatment and protection of other forms of cardiac damage, treatment and protection against stroke and its associated damage, and treatment and protection against ischemic injury to any body organ.

The treatment methods disclosed herein may be practiced in order to treat heart failure and may have a variety of advantages over existing treatment methods for treating heart failure. First, treatment of heart failure is limited to drugs that normally do not target the heart muscle, and the present disclosed treatment methods may be designed to target cardiomyocytes. Existing treatment methods do not target mitochondria for treatment of tissue damage, and the present treatment methods may be designed to target mitochondria specifically. There are currently no FDA approved drugs related to iron or iron chelators in heart failure. The presently disclosed methods may provide a novel approach to target mitochondrial iron in heart failure and ischemic injury. Finally, existing treatment methods do not differentiate between iron chelators that target the mitochondria and those that are nonspecific and reduce total cellular iron in clinical practice. The present methods may be designed to reduce baseline iron levels in mitochondrial specifically as a therapy in heart failure and myocardial infarction The disclosed methods typically include administering a mitochondrial permeable iron chelator. Iron chelators that are used for therapeutics are known in the art. (See e.g., Kalinowski et al., "The Evolution of Iron Chelators for the Treatment of Iron Overload Disease and Cancer," Pharmacological Reviews 57:547-583 (2006), the content of which is incorporate herein by reference in its entirety). Iron chelators have been used for or have been suggested for use as therapeutics in treating iron overload disease, cancer, and malaria. (See id.; and Herschko et al., Blood, Vol. 77, No. 3 (February 1), 1991: pp 637-643, the content of which is incorporate herein by reference in its entirety). Lipophilicity of iron chelators has been observed to correlate with efficacy as antiproliferative agents and anti-malarial agents. (See id.; and Richardson et al., Blood, Vol. 86, No. 11 (December 1), 1995: pp 4295-4306, the content of which is incorporate herein by reference in its entirety). Suitable mitochondrial permeable iron chelators may include, but are not limited to di-pyridyl compounds, siderophores (e.g., desferrioxamine, desferrithiocin, desferri-exochelin), ICL670A, deferiprone and hydroxypyridinone analogs (e.g., CP94, hydroxypyridinone ester prodrugs, hexadentate hydroxypyridinone analogs), tachpyridine, N-methyl-tachpyridine, aryoylhydrazones (e.g., pyridoxal isonicotinoyl hydrazone, 2-pyridylcarboxaldehyde isonicotinoyl hydrazone, di-2-pyridylketone isonicotinoyl hydrazone, and thiosemicarbazones (e.g., triapine, 2-hydroxy-1-naphthyladehyde-3-thiosemicarbazone, di-2-pyridyldetone thiosemicarbazone). Suitable specific mitochondrial permeable iron chelators may include, but are not limited to 2,2'-bipyridyl, desferri-exochelin, salicylaldehyde isonicotinoyl hydrazine, pyridoxal isonicotinoyl hydrazone, 2-hydroxy-1-naphthylaldehyde isonicotinoyl hydrazone, 2-hydroxy-1-naphthylaldehyde-4-phenyl-3-thiosemicarbazone, 3-hydroxypyridin-4-one, and 1,2-dimethyl-3-hydroxypyridin-4-one.

Preferably, the disclosed iron chelators are lipophilic in order to promote mitochondrial permeability. Lipophilicity may be measured as the partition coefficient of a molecule between an aqueous and a lipophilic phase (log P), where the aqueous phase may be water and the lipophilic phase may be octanol:

$$\log P_{oct/wat} = \log\left(\frac{[\text{solute}]_{octanol}}{[\text{solute}]_{water}^{un-ionized}}\right)$$

Preferably, the disclosed iron chelators have a log P greater than about 0, 1, 2, 3, 4, or 5, or the disclosed iron chelators have a log P within a range bounded by any of the values: 0, 1, 2, 3, 4, or 5.

It is know in the art that iron chelators may be alkylated in order to increase liphophilicity. (See Herschko et al., Blood, Vol. 77, No. 3 (February 1), 1991: pp 637-643). As such, disclosed herein are alkylated iron chelators and the use of alkylated iron chelators for treating and/or preventing cell death and organ damage following an ischemic event.

The pharmaceutical compositions disclosed herein comprising a mitochondrial permeable iron chelator may be formulated as pharmaceutical composition for administration to a subject in need thereof. Such compositions can be formulated and/or administered in dosages and by techniques well known to those skilled in the medical arts taking into consideration such factors as the age, sex, weight, and condition of the particular patient, and the route of administration.

The compositions may include pharmaceutical solutions comprising carriers, diluents, excipients, and surfactants as known in the art. Further, the compositions may include preservatives. The compositions also may include buffering agents.

The pharmaceutical compositions may be administered therapeutically. In therapeutic applications, the pharmaceutical compositions are administered to a patient in an amount sufficient to elicit a therapeutic effect (e.g., a therapeutic effect in response to an ischemic event which protects against cell death and organ damage (i.e., a "therapeutically effective dose")).

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for decreasing baseline mitochondrial iron in a subject in need thereof.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Illustrative routes of administering the compounds employed in the compositions and methods disclosed herein may include but are not limited to intravenous, oral, transdermal, percutaneous, intramuscular, intranasal, buccal, intrathecal, and intracerebral routes. The route of administration may be varied in any way, limited by the physical properties of the compounds being employed and the convenience of the subject and the caregiver.

ILLUSTRATIVE EMBODIMENTS

The following embodiments are illustrative and should not be interpreted to limit the scope of the claimed subject matter.

1. A method for treating or preventing a disease or disorder responsive to a decrease in baseline mitochondrial iron in a subject in need thereof, the method comprising administering a pharmaceutical composition comprising a mitochondrial permeable iron chelator to the subject.

2. The method of claim 1, wherein the mitochondrial permeable iron chelator is administered to the subject following an ischemic event.

3. The method of claim 1 or 2, wherein the method protects against cell death and organ damage in the subject following an ischemic event.

4. The method of any of the foregoing claims, wherein the subject has experienced or is at risk for developing cardiomyopathy, heart failure, or ischemic heart disease.

5. The method of claim 4, wherein the method protects against ischemia/reperfusion (I/R) injury in the heart.

6. The method of any of the foregoing claims, wherein the subject has experienced or is at risk for experiencing a stroke.

7. The method of claim 6, wherein the mitochondrial permeable iron chelator is administered to the subject following a stroke.

8. The method of claim 7, wherein the method protects against ischemic damage in the brain.

9. The method of any of the foregoing claims, wherein the mitochondrial permeable iron chelator is a lipophilic iron chelator.

10. The method of any of the foregoing claims, wherein the mitochondrial permeable iron chelator has a log P>1.

11. The method of any of the foregoing claims, wherein the mitochondrial permeable iron chelator is selected from the group consisting of di-pyridyl compounds, siderophores (e.g., desferrioxamine, desferrithiocin, desferri-exochelin), ICL670A, deferiprone and hydroxypyridinone analogs (e.g., CP94, hydroxypyridinone ester prodrugs, hexadentate hydroxypyridinone analogs), tachpyridine, N-methyl-tachpyridine, aryoylhydrazones (e.g., pyridoxal isonicotinoyl hydrazone, 2-pyridylcarboxaldehyde isonicotinoyl hydrazone, di-2-pyridylketone isonicotinoyl hydrazone, and thiosemicarbazones (e.g., triapine, 2-hydroxy-1-naphthylade-hyde-3-thiosemicarbazone, di-2-pyridyldetone thiosemicarbazone).

12. The method of any of the foregoing claims, wherein mitochondrial permeable iron chelator is selected from the group consisting of 2,2'-bipyridyl, desferri-exochelin, salicylaldehyde isonicotinoyl hydrazine, pyridoxal isonicotinoyl hydrazone, 2-hydroxy-1-naphthylaldehyde isonicotinoyl hydrazone, 2-hydroxy-1-naphthylaldehyde-4-phenyl-3-thiosemicarbazone, 3-hydroxypyridin-4-one, and 1,2-dimethyl-3-hydroxypyridin-4-one.

EXAMPLES

The following examples are illustrative and are not intended to limit the disclosed and claimed subject matter.

Example 1—Reducing Mitochondrial, but not Cytosolic Iron, Protects the Heart Against Ischemic-Reperfusion Injury Reference is made to Appendix III which includes the Abstract entitled "Reducing Mitochondrial, But Not Cytosolic Iron, Protects The Heart Against Ischemic-reperfusion Injury," Hsiang-Chun Chang, Rongxue Wu, and Hossein Ardehali, which was presented at the American Heart Association's Basic Cardiovascular Sciences 2014 Scientific Sessions: Pathways to Cardiovascular Therapeutics 2013 Scientific Session and Resuscitation Science Symposium, Jul. 14-17, 2014.

Introduction:

Iron is essential for the activity of a large number of cellular proteins, but excess free iron can cause cellular damage through production of reactive oxygen species (ROS). Mitochondria are the major site of cellular iron homeostasis, and we recently showed the mitochondrial iron export is mediated by ATP-binding cassette protein-B8 (ABCB8). The role of mitochondrial iron in ischemia/reperfusion (I/R) injury in the heart has not been examined We hypothesize that mitochondrial iron has a critical role in I/R damage and a reduction of mitochondrial iron is protective against I/R injury through a reduction in ROS.

Results:

Cardiomyocyte-specific ABCB8 transgenic (TG) mice had significantly lower mitochondrial iron in the heart than nontransgenic (NTG) littermates at baseline, but their cardiac function and the expression of key antioxidant systems were indistinguishable from NTG littermates. To study the role of mitochondrial iron in I/R injury, we subjected ABCB8 TG mice to I/R. TG mice displayed significantly less apoptosis compared to NTG littermates (11.76% vs. 17.63%, p<0.05, n=4-6) and had significantly reduced lipid peroxidation products 48 hours after I/R. To further confirm that our in vivo finding was due to reduced mitochondrial iron, we studied the effect of pharmacological reduction of mitochondrial iron in vitro. 2,2-bipyridyl (BPD) is a mitochondria-accessible iron chelator while deferoxamine (DFO) has poor penetrance into mitochondria. BPD has a log P of 1.5, whereas DFO has a log P of −0.614. Treating rat cardiomyoblasts H9C2 with BPD but not DFO significantly reduced chelatable mitochondrial iron, as measured by staining cells with rhodamine B-[1,10-phenanthrolin-5-yl) aminocarbonyl]benzyl ester. In addition, BPD but not DFO pretreatment protected cells against $H_2O_2$ induced cell death (p<0.05). BPD treatment in mice decreased baseline mitochondrial iron and significantly preserved cardiac function after I/R.

Conclusions:

Our findings demonstrate that selective reduction in mitochondrial iron is protective in I/R injury, and show that mitochondrial iron is a source of ROS and cellular damage in I/R. Thus, targeting mitochondrial iron with selective iron chelators, as studied in our system, may provide a novel approach for treatment of ischemic heart disease.

Example 2—A Decrease in Mitochondrial, but not Cytosolic, Iron Protects Against Cardiac Ischemia-Reperfusion Damage Through a Reduction in ROS Reference is made to Appendix II which includes the Abstract entitled "A Decrease in Mitochondrial, but Not Cytosolic, Iron Protects Against Cardiac Ischemia-Reperfusion Damage Through a Reduction in ROS," Hsiang-Chun Chang, Rongxue Wu, and Hossein Ardehali, which was presented at the American Heart Association 2014 Scientific Session and Resuscitation Science Symposium, Nov. 15-19, 2014.

Introduction:

Iron is essential for the activity of several cellular proteins, but excess free iron can cause cellular damage through production of reactive oxygen species (ROS). Iron accumulation in mitochondria, the major site of cellular iron homeostasis, leads to cardiomyopathy. However, it is not known whether a reduction in baseline mitochondrial (as opposed to cytosolic) iron can protect against ischemia-reperfusion (I/R) injury in the heart. We hypothesized that since mitochondria are the major site of iron homeostasis and that mitochondrial iron can lead to oxidative damage, a reduction in mitochondrial iron at baseline would be sufficient to protect against I/R injury.

Results:

Transgenic (TG) mice with cardiomyocyte-specific overexpression of the mitochondrial iron export protein ATP-binding cassette (ABC)-B8 had significantly lower mitochondrial iron in the heart than nontransgenic (NTG) littermates at baseline, but their cardiac function and the expression of key antioxidant systems were similar to NTG littermates. In response to I/R, TG mice displayed significantly less apoptosis and lipid peroxidation products and better preserved cardiac function than NTG littermates, suggesting that a reduction in mitochondrial iron protects against I/R injury. To confirm these results, we next took a pharmacological approach to assess the effects of a reduction in mitochondrial vs cytosolic iron on the response to I/R using 2,2'-bipyridyl (BPD, a mitochondria accessible iron chelator) and deferoxamine (DFO, an iron chelator that can only reduce cytosolic iron). Treating rat cardiomyoblast H9C2 cells with BPD but not DFO significantly lowered chelatable mitochondrial iron and protected against $H_2O_2$ induced cell death, and pretreatment with BPD but not DFO protected mice against I/R injury and reduced ROS production, suggesting that a reduction in baseline mitochondrial, but not cytosolic, iron is sufficient to protect against I/R injury.

Conclusions:

Our findings demonstrate that selective reduction in mitochondrial iron is protective in I/R injury. Thus, targeting mitochondrial iron with selective iron chelators may provide a novel approach for treatment of ischemic heart disease.

Example 3—Iron Chelator as a Treatment for Cardiomyopathy, Heart Failure, and Ischemic Heart Disease Brief Summary Heart failure remains a major health problem in this country and the incidence of this order continues to increase. There are many causes of heart failure. However, the most common cause in this country is ischemic injury to the heart. As a result of myocardial infarction, the heart muscle gets damaged and thus, the heart becomes incapable of pumping sufficient blood to the peripheral tissue. Although there are several treatments are available for both heart failure and treatment of ischemic heart disease, many of these treatments target the peripheral tissue to reduce overall physiological changes that occur because of these disorders. In case of ischemic heart disease, angioplasty and stent placement have also been utilized to treat patients. In our studies, we focused on the heart muscle and attempted to devise strategies to protect the heart muscle (the pump itself) from damage. We had previously shown that deletion of a protein involved in mitochondrial iron export (ABCB8) results in mitochondrial iron accumulation and development of cardiomyopathy (a term meaning cardiac muscle damage and the underlying cause of heart failure). We had also shown that mitochondrial iron is elevated in patients with heart failure. Thus, we hypothesized that a reduction in mitochondrial iron is protective against the development of heart failure and cardiac damage as a result of ischemic injury. We showed that a reduction of mitochondrial iron either genetically (by ABCB8 overexpression) or pharmacologically (by using iron chelators that are permeable through the membrane and can reduce mitochondrial iron) results in a decrease in ischemic injury to the heart and development of cardiomyopathy in mice. These studies were also confirmed in vitro, using isolated cardiomyocytes. Thus, our studies for the first time identify a method that targets mitochondrial iron in the heart as a therapeutic option in heart failure and in patients with ischemic heart disease.

Description

We had previously observed increased mitochondrial iron levels in tissue samples from patients with heart failure undergone cardiac transplant, and in mouse hearts after ischemia/reperfusion (I/R) damage. Furthermore, we had shown that mice that have an increased amount of mitochondrial iron (as a result of genetic deletion of a gene involved in mitochondrial iron export) develop cardiomyopathy. These studies indicate that a decrease in mitochondrial iron may be beneficial in patients with cardiovascular disease. However, clinical trials in patients had also provided evidence that iron supplementation results in an improvement of symptoms in patients with heart failure. Thus, the role of iron in cardiovascular disease remained unclear. We hypothesized that we can prevent development of heart failure and ischemic damage in the heart if we reduce mitochondrial iron. This novel hypothesis is not only aimed at patients who have iron overload in their hearts, but EVERY patient who suffers from heart failure or ischemic heart disease. To test this hypothesis, we utilized two iron chelators with distinct cellular and subcellular permeability: deferoxamine (DFO), a strong iron chelator that does not modulate mitochondrial iron, and 2,2'-bipyridyl (BPD), a lipophilic iron chelator that can penetrate into subcellular structures. We showed that mice pretreated for a week with BPD (80 mg/kg) but not DFO (50 mg/kg) have lower mitochondrial iron while both iron chelators are capable of decreasing cytosolic and nuclear iron. Similar observation has also been made in tissue culture setting. Furthermore, mice pretreated with BPD but not DFO have preserved cardiac function after I/R. To demonstrate that a decrease in mitochondrial iron alone is sufficient to confer protective effects, we also perform I/R procedure on cardiac-specific ABCB8 transgenic (TG) mice, which have lower mitochondrial iron but normal cardiac function at baseline. ABCB8 TG mice have preserved cardiac function compared to non-transgenic littermates after I/R, suggesting that modulation of mitochondrial iron alone is sufficient to reduce cardiac tissue damage from I/R. Additional mechanistic studies suggest that the protection is associated with reduced reactive oxygen species production.

Furthermore, we utilized a genetic model of mitochondrial iron overload—cardiac-specific knockout of ABCB8 to test whether modulation of mitochondrial iron can be effective in preventing the development of cardiomyopathy and progression to heart failure in these models. Normally, mice with ABCB8 deleted in the heart develop spontaneous cardiomyopathy about six weeks after deletion and progress to heart failure. We pretreated mice with BPD for 1 week before deletion of the ABCB8 gene in cardiomyocyte. The BPD treatment continued until 6 weeks after deletion. At 6 weeks after deletion, ABCB8 knockout mice receiving vehicle treatment developed cardiomyopathy while mice receiving BPD had preserved cardiac function. These results suggested that modulation of mitochondrial iron can prevent the worsening of cardiac function and development of heart failure in the setting of mitochondrial iron overload.

Conclusion

Heart failure is a disease that can be managed but cannot be effectively treated. This disorder is generally treated with drugs that reduce the neurohormonal aspects of heart failure and do not target the heart (i.e., the pump itself).

Ischemic heart disease is due to blockage of coronary vessels, mostly due to atherosclerosis. Although interventions exist to open up the blocked vessels, treatment options to protect the cardiomyocyte from ischemic damage is limited.

The present studies provide preclinical models that heart failure and ischemic heart disease, which are two very common disorders in this county and among the most common causes of death, can be treated using iron chelator that can penetrate mitochondria. The results presented here indicate that certain iron chelators have potential to treat these highly important clinical entities.

REFERENCES

1. Anker S D, Comin Colet J, Filippatos G, Willenheimer R, Dickstein K, Drexler H, Lüscher T F, Bart B, Banasiak W, Niegowska J, Kirwan B A, Mori C, von Eisenhart Rothe B, Pocock S J, Poole-Wilson P A, Ponikowski P; FAIR-H F Trial Investigators. Ferric carboxymaltose in patients with heart failure and iron deficiency. N Engl J Med. 2009 Dec. 17; 361(25):2436-48.
2. Ichikawa Y, Bayeva M, Ghanefar M, Potini V, Sun L, Mutharasan R K, Wu R, Khechaduri A, Jairaj Naik T, Ardehali H. Disruption of ABCB8 in mice leads to cardiomyopathy through a decrease in mitochondrial iron export. Proc Natl Acad Sci USA. 109(11):4152-7. 2012.
3. Jankowska E A, Malyszko J, Ardehali H, Koc-Zorawska E, Banasiak W, von Haehling S, Macdougall I C, Weiss G, McMurray J J, Anker S D, Gheorghiade M, Ponikowski P. Iron status in patients with chronic heart failure. Eur Heart J. 34(11):827-34. 2013.
4. Bayeva M, Gheorghiade M, Ardehali H. Mitochondria as a Therapeutic Target in Heart Failure. JACC. 12; 61(6): 599-610. 2013.
5. Khechaduri A, Bayeva M, Chang, H C, Ardehali H. Heme Levels are increased in human failing hearts. JACC. 7; 61(18):1884-93. 2013.
6. Ichikawa Y, Ghanefar M, Bayeva M, Wu R, Khechaduri A, Prasad S V, Mutharasan R K, Naik T J, Ardehali H. Cardiotoxicity of doxorubicin is mediated through mitochondrial iron accumulation. J Clin Invest. 124(2):617-30. 2014.

Example 4—Reduction of Mitochondrial Iron Alleviates Cardiac Damage During Injury Reference is made to Chang et al., "Reduction in mitochondrial iron alleviates cardiac damage during injury," EMBO Mol. Med. (2016) 8:247-267, the content of which is incorporated by reference in its entirety.

Title—Reduction in Mitochondrial Iron Alleviates Cardiac Damage During Injury

Abstract

Excess cellular iron increases reactive oxygen species (ROS) production and causes cellular damage. Mitochondria are the major site of iron metabolism and ROS production; however, few studies have investigated the role of mitochondrial iron in the development of cardiac disorders, such as ischemic heart disease or cardiomyopathy (CM). We observe increased mitochondrial iron in mice after ischemia/reperfusion (I/R) and in human hearts with ischemic CM, and hypothesize that decreasing mitochondrial iron protects against I/R damage and the development of CM. Reducing mitochondrial iron genetically though cardiac-specific overexpression of a mitochondrial iron export protein or pharmacologically using a mitochondria-permeable iron chelator protects mice against I/R injury. Furthermore, decreasing mitochondrial iron protects the murine hearts in a model of spontaneous CM with mitochondrial iron accumulation. Reduced mitochondrial ROS that is independent of alterations in the electron transport chain's ROS producing capacity contributes to the protective effects. Overall, our findings suggest that mitochondrial iron contributes to cardiac ischemic damage, and may be a novel therapeutic target against ischemic heart disease.

Introduction

Cardiovascular disease accounts for nearly six hundred thousand deaths per year in United States (Heron, 2013) and over four million deaths in Europe (Nichols et al., 2012), making it the most common cause of death in the Western World. While current therapies improve survival from the initial myocardial infarction (Hollenbeck et al., 2014; Simoons et al., 1986), many patients ultimately develop heart failure (Liang & Delehanty, 2009), which poses great financial burden on the healthcare system (Braunwald, 2013) and significantly diminishes quality of life. It is believed that the extent of cardiac tissue damage is correlated with the development of heart failure (Foo et al., 2005; McAlindon et al., 2015); however, no clinically available therapy directly targets cardiomyocytes in order to reduce damage after ischemia/reperfusion (I/R) injury. Therefore, the development of novel therapies targeting cardiomyocyte death is essential.

Iron is a required element for normal cellular processes, including cellular respiration (Gille & Reichmann, 2011; Hirst, 2013), protein production (Kispal et al., 2005), lipid metabolism (Shakoury-Elizeh et al., 2010), and DNA replication (Furukawa et al., 1992). Normally, iron is used for heme and iron/sulfur (Fe/S) cluster synthesis in mitochondria or is stored in ferritin molecules in the cytoplasm (De Domenico et al., 2008; Hentze et al., 2010; Ye & Rouault, 2010) or in mitochondrial ferritin molecules in mitochondria (Horowitz & Greenamyre, 2010; Li et al., 2014; Napier et al., 2005; Vigani et al., 2013). Excess iron can cause tissue damage through the production of reactive oxygen species (ROS) via the Fenton-like and Harbor-Weiss reactions (Aigner et al., 2008). Iron-catalyzed ROS formation can also increase free iron through reactions with Fe/S clusters or other forms of loosely-bound iron (Gomez et al., 2014; Sideri et al., 2009). Previous studies have demonstrated a role for lysosomal iron in radiation-mediated or $H_2O_2$-induced cell death (Kurz et al., 2010; Persson et al., 2005; Yu et al., 2003). Additionally, in diseases with mitochondrial iron overload, iron-mediated mitochondrial DNA and membrane damage has been linked to mitochondrial dysfunction (Eaton & Qian, 2002; Gao et al., 2009).

Increased iron has been described in the setting of I/R in various organs (Comporti et al., 2002; Ghio, 2009; Kaushal & Shah, 2014; Zhao et al., 1997), and increased transferrin receptor 1 expression due to activation of hypoxia inducible factor signaling has been implicated as a mechanism for the change in cellular iron (Tang et al., 2008). While one study suggested that extracellular iron is involved in renal I/R injury (de Vries et al., 2004), very few studies have discerned the contribution of baseline iron in various subcellular compartments to I/R injury in cells and animals.

Because of iron's contribution to ROS production, several studies have evaluated the efficacy of iron chelation in alleviating tissue damage during myocardial infarction, but the results have been controversial. Deferoxamine (DFO), a Federal Food and Drug Administration approved iron chelator for transfusion-related iron overload, has a strong affinity for iron but low cellular permeability. DFO treatment was shown to improve cardiac function after I/R in an ex vivo heart perfusion system (Badylak et al., 1987; Nicholson et al., 1997; Williams et al., 1991), and in canine and porcine models of I/R in vivo (Chopra et al., 1992; Kobayashi et al., 1991; Lesnefsky et al., 1990b; Ramesh Reddy et al., 1989). Infusion of DFO was also associated with improved cardiac function in patients who had undergone coronary artery bypass surgery (Menasche et al., 1990; Paraskevaidis et al., 2005), and iron chelation with DFO in patients with thalassemia major led to improved cardiac function and survival (Marcus et al., 1984; Pepe et al., 2011; Porter et al., 2013). On the other hand, some reports using DFO in large animal models or primate models of I/R failed to reduce the infarct size after injury (Chatziathanasiou et al., 2012; Lesnefsky et al., 1990a; Watanabe et al., 1993). Tissue penetrance was cited as a potential cause of the lack of protective effects. This explanation is further supported by the ability of another cell-permeable iron chelator, 2,2'-bipyridyl (BPD), to protect rats against cerebral infarction (Demougeot et al., 2004; Methy et al., 2008; Wu et al., 2012). It should also be noted that these studies all assessed the effects of iron chelation on total cellular iron, and did not distinguish iron in different subcellular compartments.

Taken together, these studies indicate that differential cellular iron localization in the heart may have functional consequences in cardiovascular disease. In the current paper, we observed an increase in mitochondrial iron after cardiac I/R injury in mice and in cardiac tissue samples from patients with ischemic cardiomyopathy (CM) compared to non-failing hearts, which led us to hypothesize that reducing baseline mitochondrial iron would protect the heart against I/R injury and the development of CM. We show that pharmacologic reduction of baseline mitochondrial iron, but not cytoplasmic iron, protects cells against $H_2O_2$-induced cell death. Our in vivo data with two distinct approaches of mitochondrial iron modulation clearly indicate that a decrease in baseline mitochondrial iron is protective against cardiac I/R injury Importantly, mice with a modest decrease in cardiac mitochondrial iron display a normal phenotype at baseline. We also demonstrate that pharmacological reduction of mitochondrial iron prevents the development of cardiomyopathy in a genetic model of mitochondrial iron overload, thus providing clinical relevance for targeting mitochondrial iron. The protective effects of reducing mitochondrial iron in both disease models are associated with reduced ROS production during injury.

Results

Mitochondrial Non-Heme Iron Increases after I/R Injury and in Human Samples with Ischemic Cardiomyopathy.

To investigate the acute changes in iron content in different subcellular localizations after I/R injury, we subjected wild-type mice to I/R and measured cytoplasmic and mitochondrial non-heme iron in the hearts of mice two days after I/R. We first verified the purity of the subcellular fractions (FIG. 10). While no significant changes in cytoplasmic non-heme iron were observed (FIG. 1A), mitochondrial non-heme iron was significantly increased after I/R injury (FIG. 1B). Since labile iron can catalyze the formation of ROS, which in turn further increases free iron, we measured chelatable mitochondrial and cytoplasmic iron in H9c2 cardiomyoblasts exposed to $H_2O_2$, a model designed to simulate the surge of ROS during the reperfusion stage of I/R. The treatment of $H_2O_2$ for 6 hours significantly increased mitochondrial chelatable iron as well as cytoplasmic chelatable iron (FIG. 1C-D). To put these findings into a clinical context, we measured mitochondrial and cytosolic non-heme iron in cardiac tissue samples from patients without heart failure and with ischemic cardiomyopathy (ISCM). Western blotting results demonstrated the purity of subcellular fractions (FIG. 10B). Mitochondrial fractions from ISCM samples had a significantly higher level of non-heme iron, while no significant difference was observed in cytosolic non-heme iron between non-failing and ISCM heart samples (FIG. 1E-F). These findings together suggest that mitochondrial non-heme iron increases after I/R and may participate in tissue injury.

A Decrease in Baseline Mitochondrial Iron Protects Cardiomyocytes Against $H_2O_2$-Induced Cell Death In Vitro.

Figure 2:
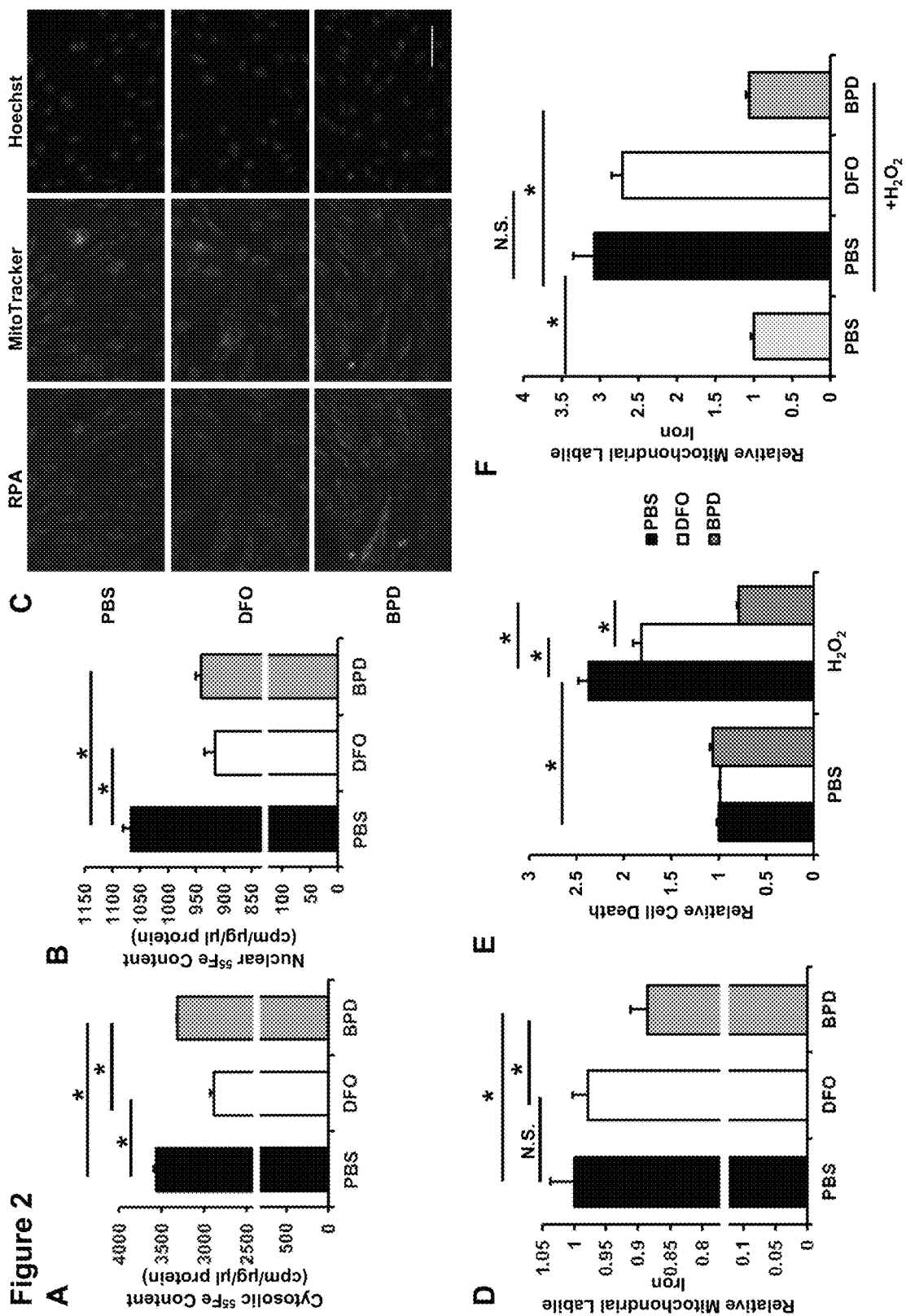
FIG. 2. Mitochondrial-permeable iron chelator is protective against oxidative stress in vitro. A. Cytosolic iron in H9c2 cells preloaded with radioactive 55Fe and treated with indicated iron chelators. * P<0.05. N=4-6 for each group. B. Nuclear iron in H9c2 cells preloaded with radioactive 55Fe and treated with indicated iron chelators. * P<0.05. N=4-6 for each group. C. Representative RPA fluorescence staining for labile mitochondrial iron in H9c2 cells with indicated iron chelator treatment. Scale bar=100 μm. D. Labile mitochondrial iron measured by RPA fluorescence in H9c2 cells with indicated iron chelator treatment. * P<0.05. N=8-12 for each group. E. $H_2O_2$-induced cell death in H9c2 cells with indicated treatments. * P<0.05. N=4-6 for each group. F. Labile mitochondrial iron in H9c2 cells with indicated treatment. PBS with and without $H_2O_2$ data were copied from FIG. 1C. * P<0.05. N=8-12 for each group.
Figure 11:
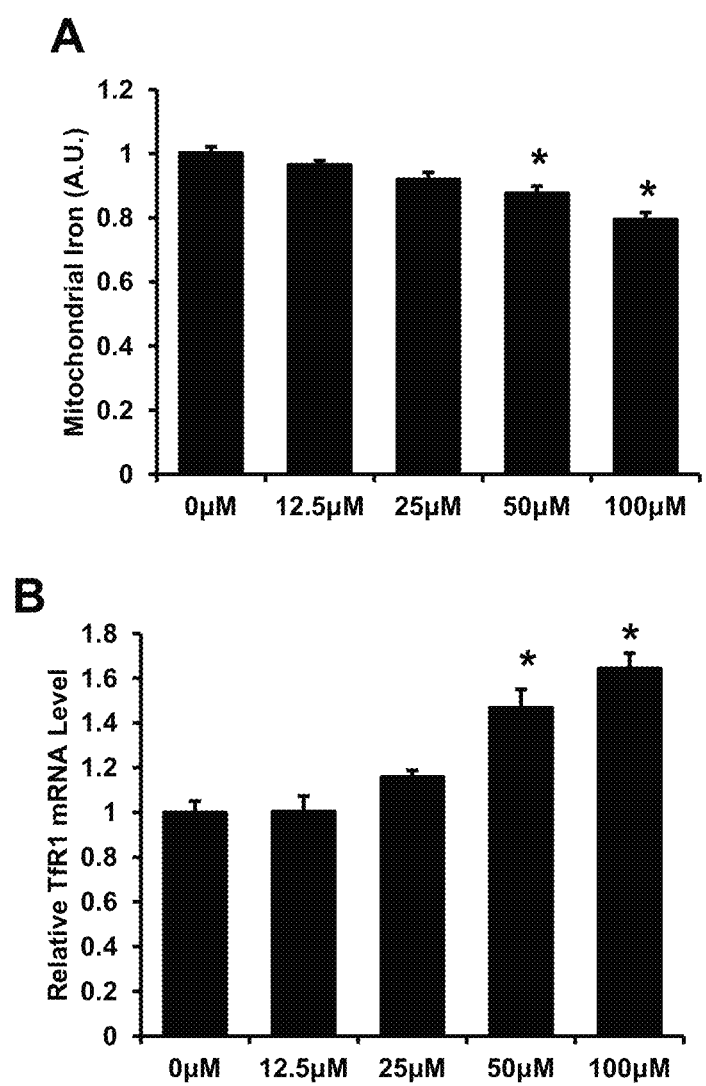
FIG. 11. Mitochondrial iron and TfR1 mRNA in response to BPD treatment in H9c2 cells. A. Mitochondrial iron levels in H9c2 cells treated with various doses of BPD. * P<0.05. N=6 in each group. B. TfR1 expression, which increases in response to a decrease in cellular iron, in cells treated with various doses of BPD. * P<0.05 compared to no treatment. N=6 in each group.

Our findings that mitochondrial non-heme iron is increased in the hearts of mice after I/R and failing human hearts and previous observations that labile iron can catalyze the conversion of hydrogen peroxide to the hydroxyl radical, a major source of tissue damage during I/R (Zweier & Talukder, 2006), prompted us to hypothesize that modulation of mitochondrial iron may protect against I/R injury. We chose two iron chelators with distinct mitochondrial permeability. DFO, which has poor penetrance through the cell membrane, and BPD, which has high membrane permeability and thus is able to access mitochondria (Demougeot et al., 2004). The dose of DFO treatment was based on previous published reports (Ichikawa et al., 2014). Various doses of BPD were tested for its ability to reduce cellular and mitochondrial iron (FIG. 11). Based on the changes in mitochondrial iron levels in cells treated with various doses of BPD, we used 100 µM of BPD for subsequent in vitro studies. DFO and BPD caused significant decreases in both cytosolic and nuclear iron (FIG. 2A-B); however, two-hour pretreatment of H9c2 cardiomyoblasts with BPD, but not DFO, decreased mitochondrial labile iron (FIG. 2C-D). While pretreatment of H9c2 with DFO only conferred a slight protection against oxidative stress, BPD pretreatment significantly reversed $H_2O_2$-induced cell death (FIG. 2E). Additionally, the increase in mitochondrial labile iron after $H_2O_2$ treatment was attenuated by BPD but not DFO treatment (FIG. 2F). Therefore, BPD, which can reduce mitochondrial iron, exerts protection against oxidative damage to the cell.

Overexpression of ABCB8 in Cardiomyocytes In Vivo Reduces Mitochondrial Iron and Protects Against I/R Damage.

Figure 3:
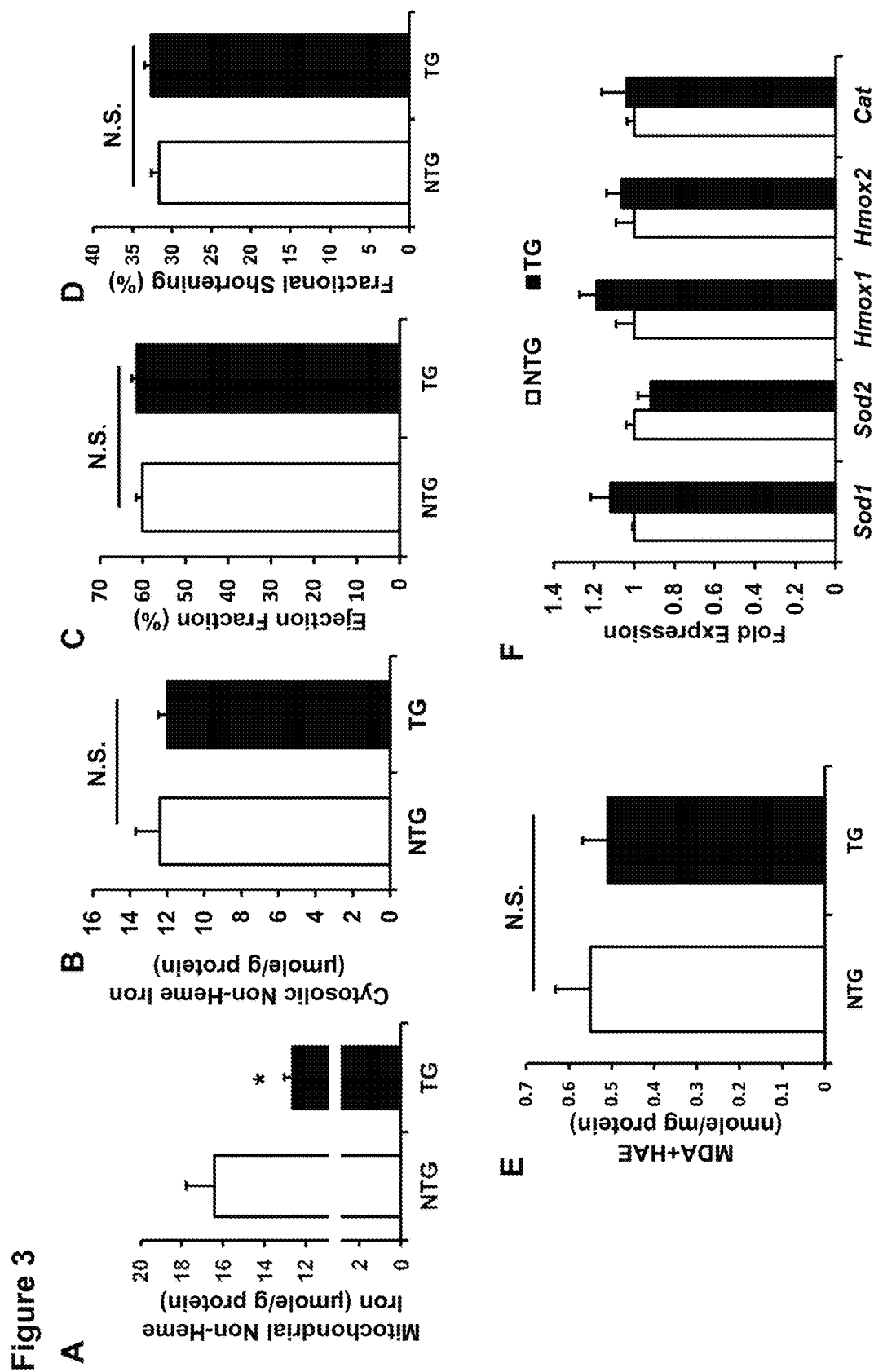
FIG. 3. Cardiac-specific ABCB8 overexpression reduces mitochondrial iron but does not alter cardiac function, ROS or the antioxidant system. A. Mitochondrial non-heme iron in ABCB8 NTG and TG mice. N=4-6 for each group. * P<0.05. B. Cytosolic non-heme iron in ABCB8 NTG and TG mice. N=4-6 for each group. C. Baseline ejection fraction of littermate ABCB8 NTG and TG mice. N=6 in each group. D. Baseline fractional shortening of littermate ABCB8 NTG and TG mice. N=6 in each group. E. Lipid peroxidation products in hearts of TG and NTG mice. N=6 in each group. F. Relative expression of antioxidant genes in NTG and TG mice. N=6 in each group.
Figure 12:
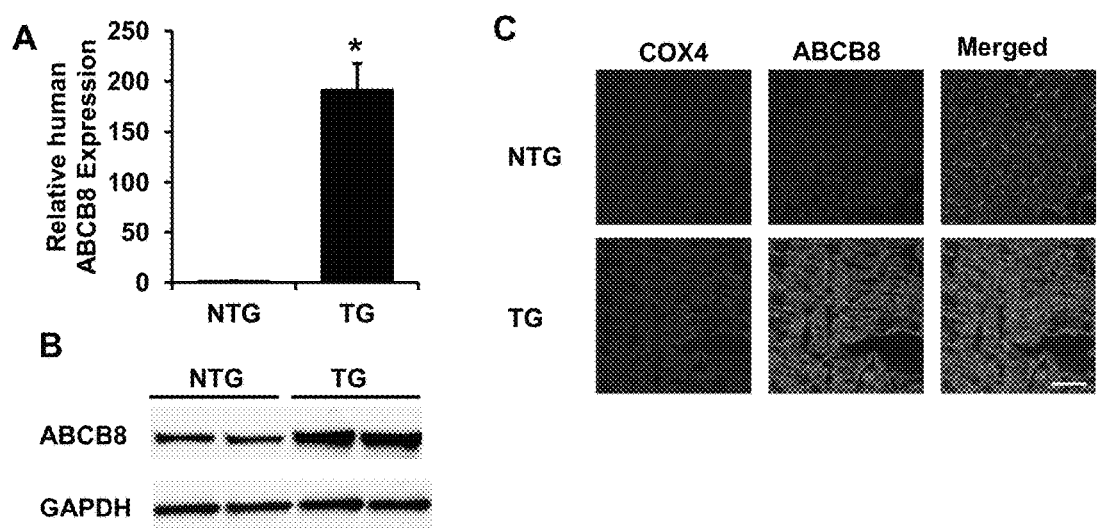
FIG. 12. ABCB8 levels in the hearts of cardiac-specific ABCB8 transgenic mice. A. mRNA levels of human ABCB8 in NTG and TG mouse hearts. N=6 for each group. * P<0.05. B. ABCB8 protein levels in NTG and TG mouse hearts. C. Representative confocal images from ABCB8 NTG and TG hearts staining for ABCB8 and COX4. Scale bar=50 μm.

Since modulation of mitochondrial iron protected cells against $H_2O_2$-induced cell death, we then tested whether similar protective effects could be observed in vivo using a cardiac I/R injury model. Previous in vitro studies demonstrated that overexpression of ABCB8, a protein found to be involved in mitochondrial iron export, decreases mitochondrial iron (Ichikawa et al., 2012). We therefore used cardiac-specific overexpression of human ABCB8 driven by α-MHC promoter as a genetic model for decreased mitochondrial iron. We first verified overexpression of ABCB8 using quantitative real-time PCR against human ABCB8 and western blotting (FIG. 12A-B) and colocalization with mitochondria using confocal microscopy (FIG. 12C). Consistent with the in vitro findings, the hearts of ABCB8 transgenic (TG) mice displayed lower mitochondrial non-heme iron levels at baseline without a significant difference in cytosolic non-heme iron levels (FIG. 3A-B). ABCB8 TG mice demonstrated normal cardiac function at baseline (FIG. 3C-D), and no change in ROS production (FIG. 3E). In addition, the expression of key antioxidant systems, including Sod1 and Sod2, in TG mice was similar to non-transgenic (NTG) littermates (FIG. 3F).

Figure 4:
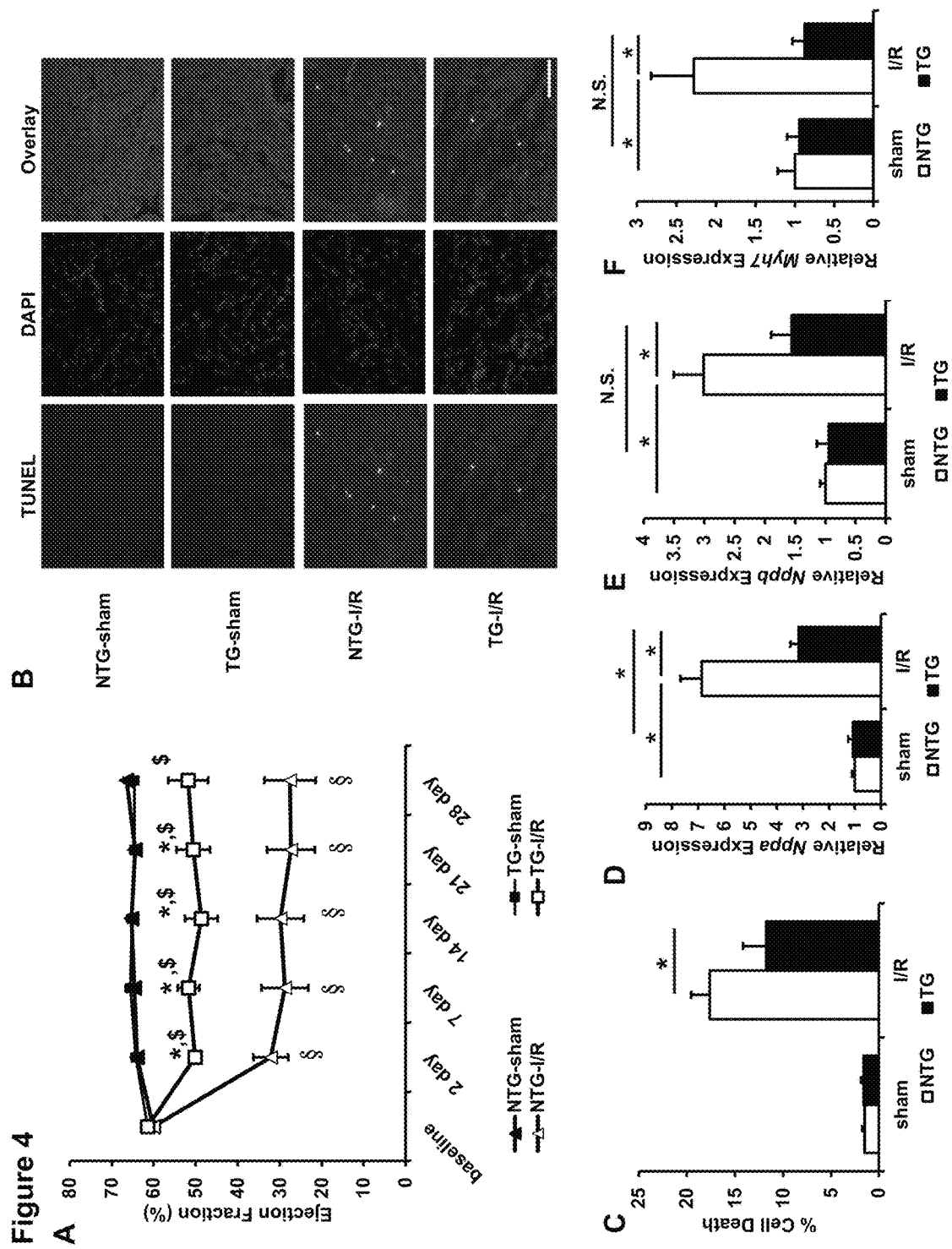
FIG. 4. ABCB8 transgenic mice have less cell death and better cardiac function after I/R injury. A. Cardiac function in ABCB8 NTG and TG mice undergoing sham or I/R procedure. * P<0.05 compared with TG-sham. $ P<0.05 compared with NTG-I/R. § P<0.05 compared with NTG-sham. N=4-6 in each group. B. Representative images of TUNEL staining for mice with indicated genotype undergone indicated procedure. Scale bar=100 μm. C. Quantification of apoptosis in ABCB8 TG and NTG mice with indicated procedure. * P<0.05. N=4-6 in each group. D. Nppa expression in mice subjected to sham or I/R procedure. * P<0.05. N=4-6 in each group. E. Nppb expression in mice subjected to sham or I/R procedure. * P<0.05. N=4-6 in each group. F. Myh7 expression in mice subjected to sham or I/R procedure. * P<0.05. N=4-6 in each group.
Figure 5:
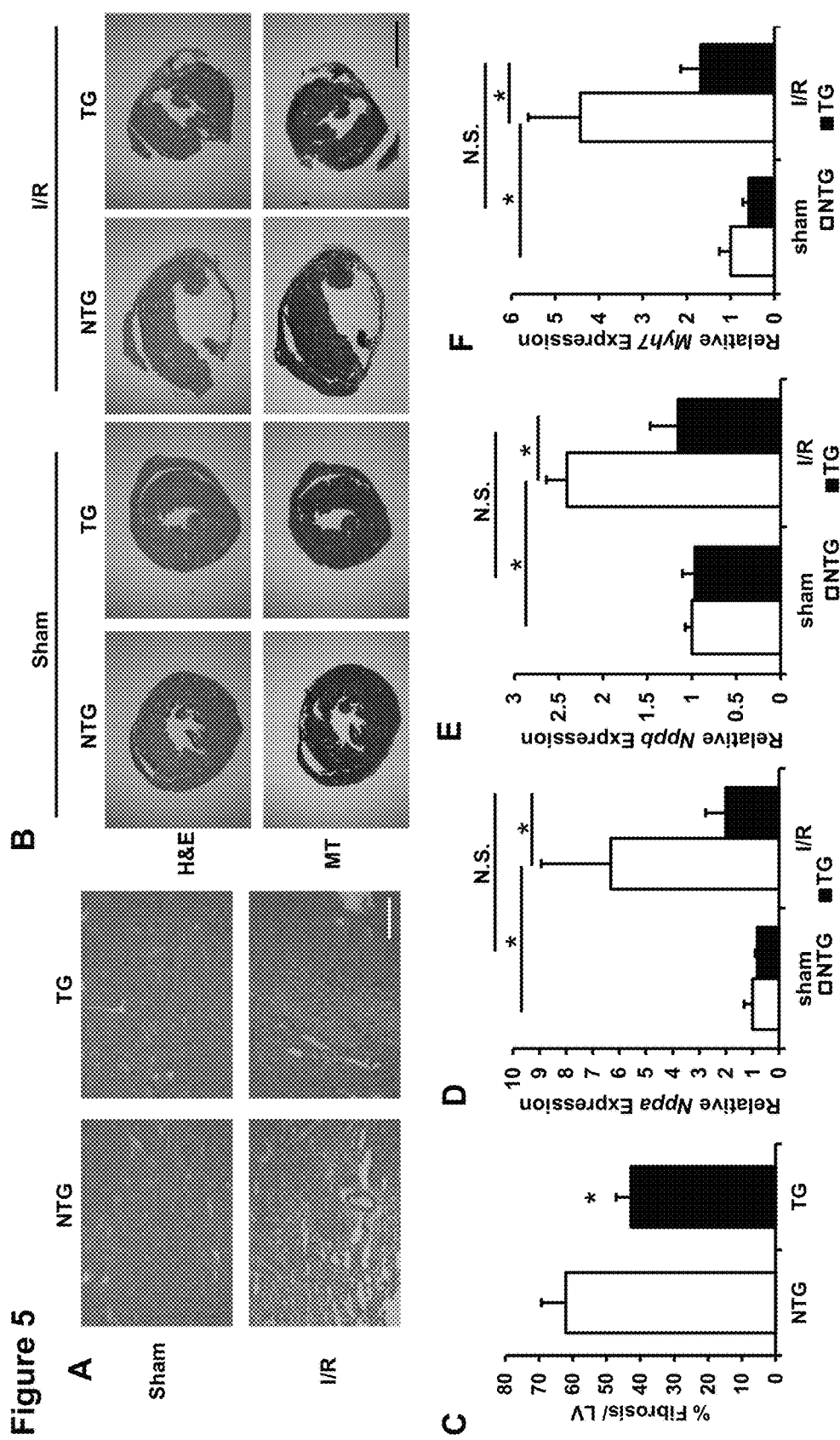
FIG. 5. ABCB8 transgenic mice demonstrate reduced acute cellular injury and decreased left ventricular fibrosis and cardiac stress 28 days after injury. A. Representative H&E staining of peri-infarct area demonstrated reduced cellular injury in ABCB8 TG mice after I/R. Scale bar=115 μm. B. Representative H&E and Masson Trichrome (MT) staining in mouse heart 28 days after indicated procedure. Scale bar=1100 μm. C. Quantification of tissue fibrosis in ABCB8 NTG and TG mice subjected to I/R. * P<0.05. N=4-6 in each group. D. Nppa expression in mice subjected to sham or I/R procedure. * P<0.05. N=4-6 in each group. E. Nppb expression in mice subjected to sham or I/R procedure. * P<0.05. N=4-6 in each group. F. Myh7 expression in mice subjected to sham or I/R procedure. * P<0.05. N=4-6 in each group.
Figure 13:
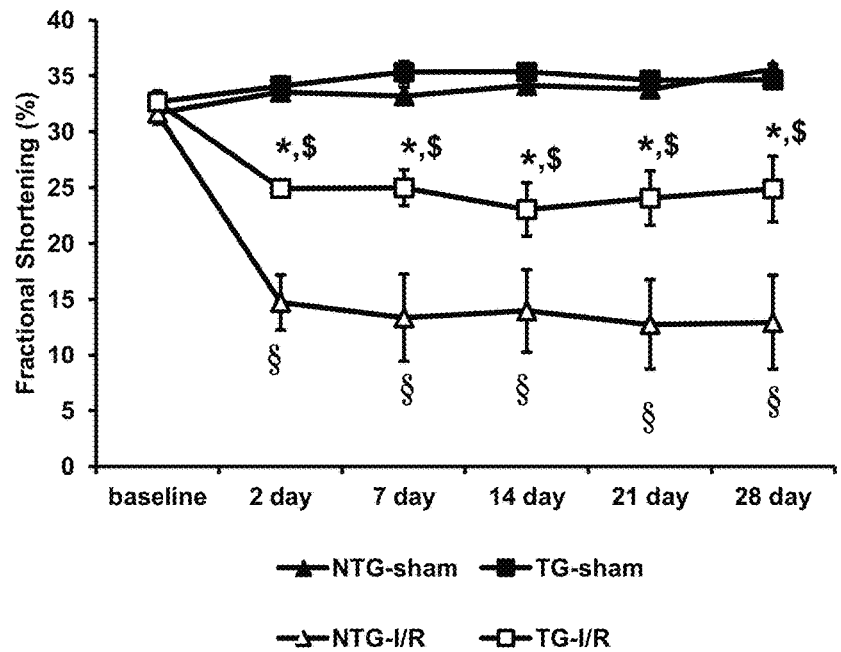
FIG. 13. Cardiac function as assessed by fractional shortening in NTG and ABCB8 TG mice after I/R. * P<0.05 compared with TG-sham. $ P<0.05 compared with NTG-I/R. § P<0.05 compared with NTG-sham. N=4-6 in each group.

We then subjected age-matched ABCB8 TG and NTG littermate mice to I/R or sham operation and monitored their cardiac function with serial echocardiography. No difference in cardiac function was observed in mice receiving the sham operation, while ABCB8 TG mice displayed significantly better cardiac function compared to NTG littermates after I/R (FIG. 4A and FIG. 13). Two days after I/R, cell death was significantly lower in ABCB8 TG mice compared to NTG littermates (FIG. 4B-C). Also, compared to NTG mice, ABCB8 TG mice demonstrated less expression of cardiac stress markers atrial natriuretic factor (Nppa), brain natriuretic peptide (Nppb) and β-myosin heavy chain (Myh7) during the acute phase of I/R injury (FIG. 4D-F). Lastly, hematoxylin and eosin staining in the peri-infarct zone revealed reduced cellular damage in ABCB8 TG mice compared to NTG mice (FIG. 5A). These results are consistent with reduced cardiac stress in ABCB8 TG mice compared to NTG mice after I/R injury.

We also studied the long-term remodeling of cardiac tissues after I/R, which was used as a proxy for estimating initial cellular damage. At 28 days after I/R, ABCB8 TG mice demonstrated significantly lower fibrosis compared to their NTG littermates (FIG. 5B-C). In addition, ABCB8 TG mice maintained reduced expression of Nppa, Nppb and Myh7 at the same time point (FIG. 5D-F), consistent with reduced cardiac stress from the initial injury. These findings further support our hypothesis that decreasing baseline mitochondrial iron in cardiomyocytes is sufficient to protect against I/R injury.

Pharmacological Modulation of Mitochondrial Iron In Vivo Protects Against I/R Damage.

Figure 6:
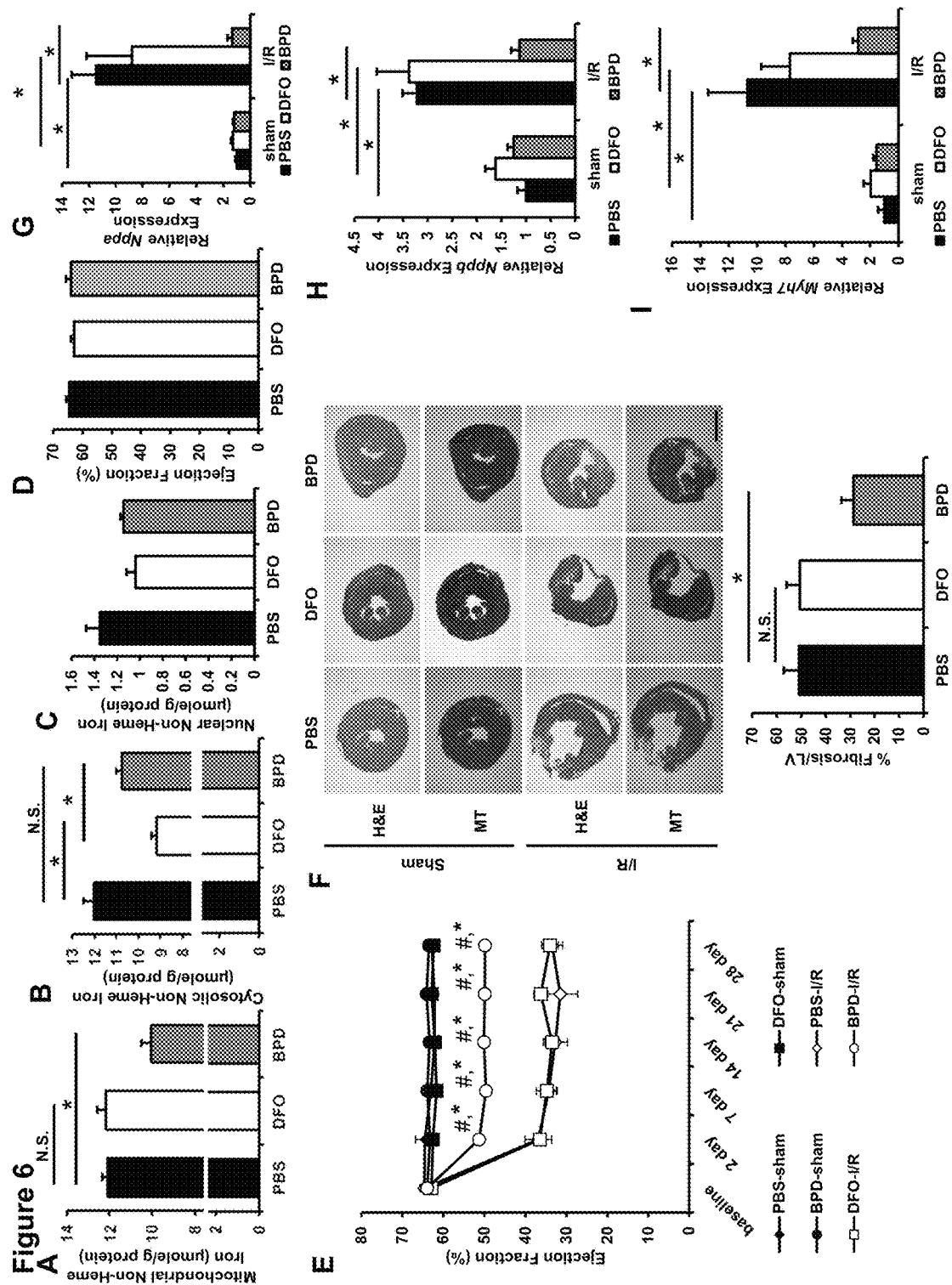
FIG. 6. Pharmacological modulation of mitochondrial iron protects against cellular damage after I/R. A. Mitochondrial non-heme iron in wild-type mice treated with vehicle control or indicated iron chelator for 7 days. * P<0.05. N=4-5 for each group. B. Cytosolic non-heme iron in wild-type mice treated with vehicle control or indicated iron chelator for 7 days. * P<0.05. N=4-5 for each group. C. Nuclear non-heme iron in wild-type mice treated with vehicle control or indicated iron chelator for 7 days. N=4-5 for each group. D. Cardiac function in wild-type mice treated with vehicle control or indicated iron chelator for 7 days. N=5 for each group. E. Cardiac function of chelator-treated mice after I/R. * P<0.05 compared to PBS-I/R group. # P<0.05 compared to PBS-sham group. N=5-6 for each group. F. Representative Hematoxylin & Eosin (H&E) and Masson Trichrome (MT) staining of heart sections in mice with indicated chelator treatment undergone sham or I/R. Scale bar=1100 μm. Bar graph represents quantification of tissue fibrosis. * P<0.05. N=4-6 for each group. G. Nppa expression in mice subjected to sham or I/R procedure. * P<0.05. N=4-6 in each group. H. Nppb expression in mice subjected to sham or I/R procedure. * P<0.05. N=4-6 in each group. I. Myh7 expression in mice subjected to sham or I/R procedure. * P<0.05. N=4-6 in each group.
Figure 14:
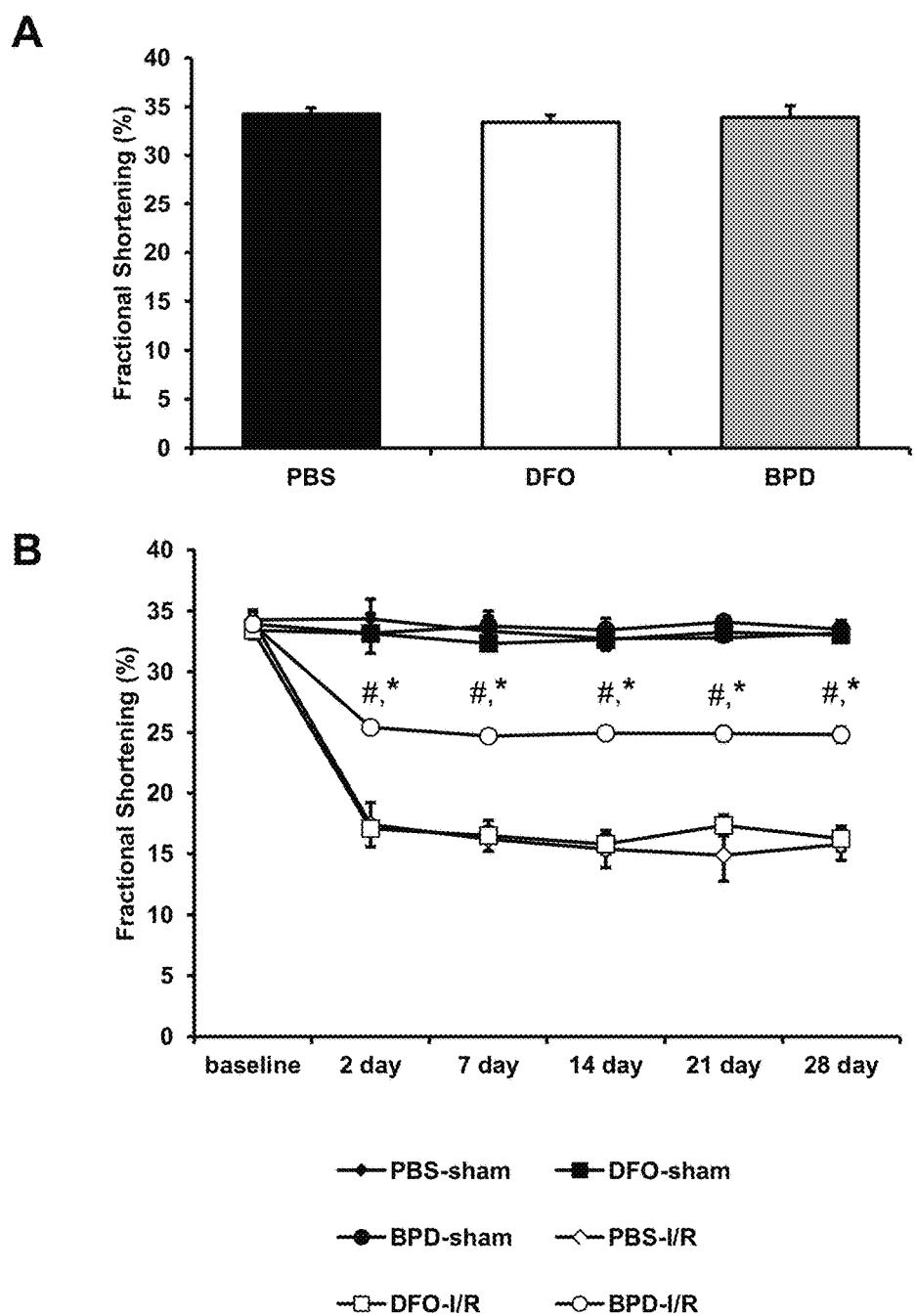
FIG. 14. Cardiac function in mice treated with iron chelators at baseline and after I/R. A. Fractional shortening in wild-type mice treated with indicated iron chelator for a week. N=5 in each group. B. Fractional shortening in wild-type mice pretreated with indicated iron chelator at different time points after I/R. * P<0.05 compared to PBS-I/R group. # P<0.05 compared to PBS-sham group. N=5-6 for each group.

Our findings demonstrate that a decrease in mitochondrial iron (using a genetic mouse model) is protective against cardiac I/R injury. To provide more clinical applicability to our findings, we used the two iron chelators (DFO and BPD) from our in vitro studies and injected them into wild-type mice prior to I/R to evaluate whether a pharmacological decrease in mitochondrial iron is sufficient to protect against I/R injury. After a one-week regimen, BPD treatment (80 mg/kg per day) in mice at baseline decreased cardiac mitochondrial iron, while DFO treatment (50 mg/kg every other day) did not alter mitochondrial iron levels (FIG. 6A). This finding is similar to our in vitro results. The inability of DFO to modulate mitochondrial iron was not due to its inactivity, as both treatments lowered cardiac cytosolic iron (FIG. 6B). A decrease in cardiac nuclear iron was also observed but did not reach statistical significance with either of the iron chelators (FIG. 6C), which can be due to relatively low amounts of iron in the nucleus (as seen comparing FIG. 2A and FIG. 2B) and the colorimetric measurement having lower sensitivity compared to the radioactive measurement. The purity of the nuclear fraction was verified with western blotting (FIG. 10C). This finding is consistent with DFO being a strong iron chelator but having poor penetrance into mitochondria. Both drugs did not cause damage to the heart at baseline as assessed by cardiac ejection fraction and fractional shortening using echocardiography (FIG. 6D and FIG. 14A).

To test the use of these iron chelators in the setting of I/R, mice were pretreated for a week with these chelators and then subjected to I/R or sham operation. Chelation was continued for two weeks after the operation. Mice treated with BPD had preserved cardiac function after I/R, while DFO failed to protect mice against I/R damage (FIG. 6E and FIG. 14B). BPD-treated mice demonstrated less cardiac remodeling compared to either vehicle- or DFO-treated mice, which is consistent with milder cardiac damage during I/R (FIG. 6F). Additionally, BPD but not DFO treatment attenuated the expression of Nppa, Nppb and Myh7 (FIG. 6G-I). To rule out any changes of serum iron hematopoiesis that can account for the cardiac functional difference, we performed complete blood counts and measured serum iron parameters in wild-type mice treated with iron chelators for 3 weeks. As expected, the three-week iron chelation regimen resulted in lower serum iron, but did not alter erythropoiesis as evidenced by comparable RBC count and hemoglobin level (Table 1).

TABLE 1

Complete blood count and serum iron parameters in wild-type mice with indicated chelator treatment (n = 5 in each group)

|  | PBS | DFO | BPD |
|---|---|---|---|
| RBC ($10^6$/μL) | 9.02 ± 0.34 | 9.77 ± 0.43 | 10.7 ± 0.62 |
| Hemoglobin (g/dL) | 11.66 ± 0.46 | 12.96 ± 0.53 | 13.12 ± 0.30 |
| Hematocrit (%) | 42.42 ± 1.55 | 47.02 ± 2.25 | 47.53 ± 1.84 |
| MCV (fL) | 47.06 ± 0.54 | 48.1 ± 0.31 | 47.02 ± 0.36 |
| MCH (pg) | 12.92 ± 0.13 | 13.28 ± 0.12 | 12.38 ± 0.53 |
| MCHC (g/dL) | 27.52 ± 0.59 | 27.62 ± 0.32 | 26.34 ± 1.21 |
| RDW (%) | 16.2 ± 0.2 | 17 ± 0.32 | 17 ± 0.41 |
| WBC ($10^3$/μL) | 5.64 ± 0.97 | 6.62 ± 0.85 | 5.70 ± 0.40 |
| Platelet ($10^3$/μL) | 629.6 ± 128.61 | 711.6 ± 139.86 | 1007 ± 236.72 |
| Serum Iron (μg/dL) | 77.62 ± 5.38 | 53.37 ± 6.63* | 44.40 ± 2.24* |
| Unsaturated Iron Binding Capacity (μg/dL) | 200.96 ± 12.56 | 227.85 ± 7.71 | 247.02 ± 4.93* |
| Total Iron Binding Capacity (μg/dL) | 278.58 ± 10.63 | 281.21 ± 12.76 | 291.42 ± 4.63 |
| Iron Saturation (%) | 28.07 ± 2.24 | 18.66 ± 1.68* | 15.25 ± 0.81* |

*$P < 0.05$ compared to PBS treated group.

These observations suggest that pharmacologically lowering mitochondrial iron levels in the setting of I/R results in protective effects.

A Decrease in Mitochondrial Iron at Baseline Protects Against the Development of Spontaneous Cardiomyopathy in Cardiac-Specific ABCB8 Knockout Mice.

Figure 7:
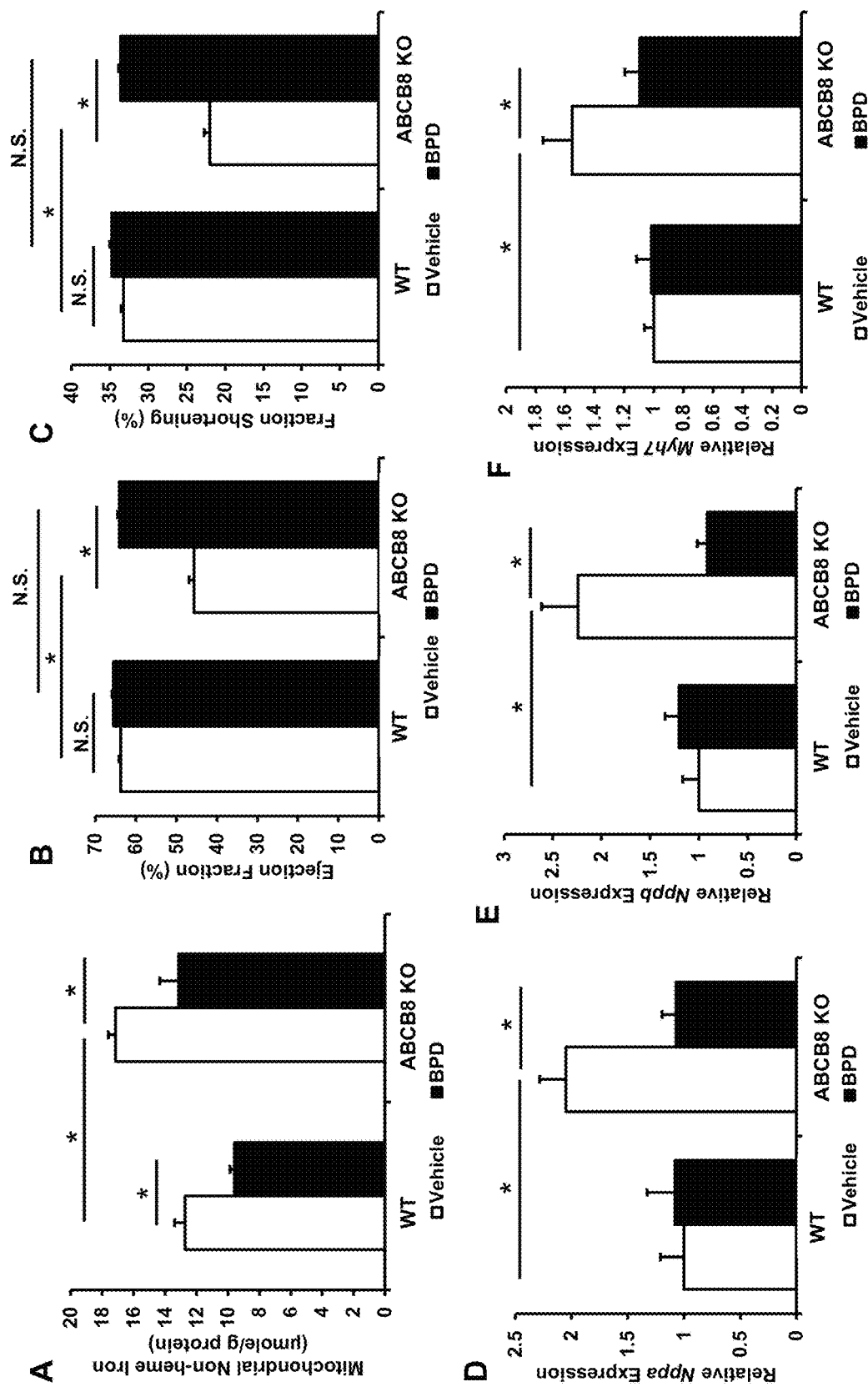
FIG. 7. A decrease in mitochondrial iron at baseline protects against the development of cardiomyopathy in inducible cardiac-specific ABCB8 knockout mice. A. Cardiac mitochondrial iron in ABCB8 KO and WT mice with indicated treatment harvested 4 weeks after the tamoxifen treatment. * P<0.05. N=6-8 for each group. B. Ejection fraction in ABCB8 KO and WT mice with indicated treatment 4 weeks after gene knockout. * P<0.05. N=6-8 for each group. C. Fractional shortening in ABCB8 KO and WT mice with indicated treatment 4 weeks after gene knockout. * P<0.05. N=6-8 for each group. D. Nppa expression in mice subjected to sham or I/R procedure. * P<0.05. N=6-8 in each group. E. Nppb expression in mice subjected to sham or I/R procedure. * P<0.05. N=6-8 in each group. F. Myh7 expression in mice subjected to sham or I/R procedure. * P<0.05. N=6-8 in each group.
Figure 15:
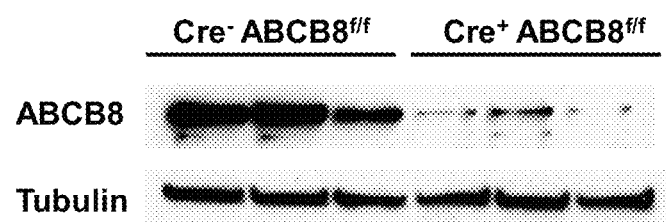
FIG. 15. Deletion of ABCB8 in cardiac-specific ABCB8 knockout mice. ABCB8 protein levels in Cre− ABCB8f/f (referred to as WT in the manuscript) and Cre+ ABCB8f/f mice (referred to as KO in the manuscript) hearts after two weeks of tamoxifen treatment.

The above studies demonstrated that a reduction in baseline mitochondrial iron is protective against I/R injury. We next took a loss-of-function approach, and studied whether a decrease in mitochondrial iron in cardiac-specific ABCB8 knockout mice, a model of spontaneous cardiomyopathy with mitochondrial iron overload (Ichikawa et al., 2012), protects against cardiac tissue damage. Because our above studies indicated that DFO does not modulate mitochondrial iron and ABCB8 knockout mice did not show cytoplasmic iron accumulation, we exclusively used BPD in the subsequent experiments. Mitochondrial iron in ABCB8 flox/flox (LoxP sequence flanking exon one of both alleles of ABCB8) mice with or without the αMHC-MER-Cre-MER transgene was modulated with BPD or vehicle control for one week before the induction of ABCB8 deletion with tamoxifen. BPD treatment continued until four weeks after the completion of tamoxifen treatment, at which point mitochondrial iron and cardiac function were measured. The effectiveness of Cre-mediated gene excision was confirmed at the protein level (FIG. 15). Cre+ mice (ABCB8 knockout, KO) receiving vehicle treatment demonstrated mitochondrial iron accumulation, while BPD treatment prevented the development of iron accumulation. BPD treatment also resulted in a decrease in mitochondrial iron in Cre-mice (WT, FIG. 7A). BPD treatment in ABCB8 KO mice preserved cardiac function, while the treatment itself was not cardiotoxic (FIG. 7B-C). Additionally, BPD-treated ABCB8 KO mice demonstrated attenuated expression of Nppa, Nppb and Myh7, which are upregulated in cardiomyopathy (FIG. 7D-F). These findings indicate that prevention of mitochondrial iron accumulation through a pharmacological approach delays the development of cardiomyopathy in an animal model of mitochondrial iron accumulation.

Modulation of Mitochondrial Iron Influences the Formation of Reactive Oxygen Species and Mitochondrial Complex Activity after Oxidative Stress.

Figure 8:
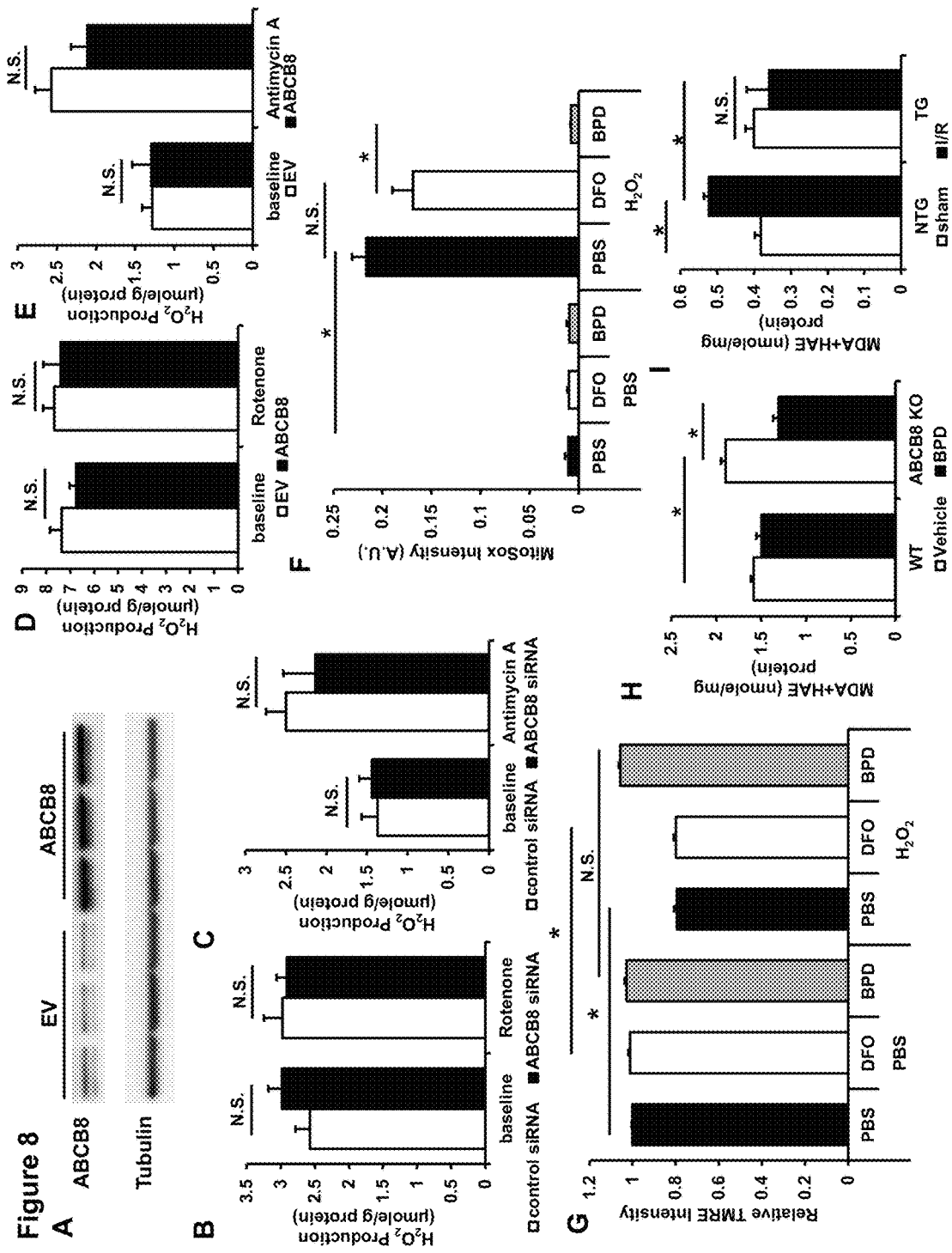
FIG. 8. Modulation of mitochondrial iron influences the production of mitochondrial ROS. A. Representative western blot demonstrating ABCB8 overexpression in H9c2 cells. EV=empty vector. N=3 for each group. B. Complex I ROS production in mitochondria with ABCB8 downregulation with or without rotenone. N=6 for each group. C. Complex III ROS production in mitochondria with ABCB8 downregulation with or without antimycin A. N=6 for each group. D. Complex I ROS production in mitochondria with ABCB8 overexpression with or without rotenone. EV=empty vector. N=8-12 for each group. E. Complex I ROS production in mitochondria with ABCB8 overexpression with or without rotenone. EV=empty vector. N=8-12 for each group. F. Mitochondrial ROS in H9c2 cells with various treatments with or without oxidative stress. N=6 for each group. * P<0.05. G. Mitochondrial membrane potential as measured by TMRE intensity in H9c2 cells treated with indicated iron chelator with or without oxidative stress. N=6 for each group. * P<0.05. H. The levels of lipid peroxidation products in ABCB8 KO mice with or without chelator treatment. N=4-6 in each group. * P<0.05. I. Lipid peroxidation products in ABCB8 TG and NTG mice two days after I/R. N=4-6 in each group. * P<0.05.
Figure 9:
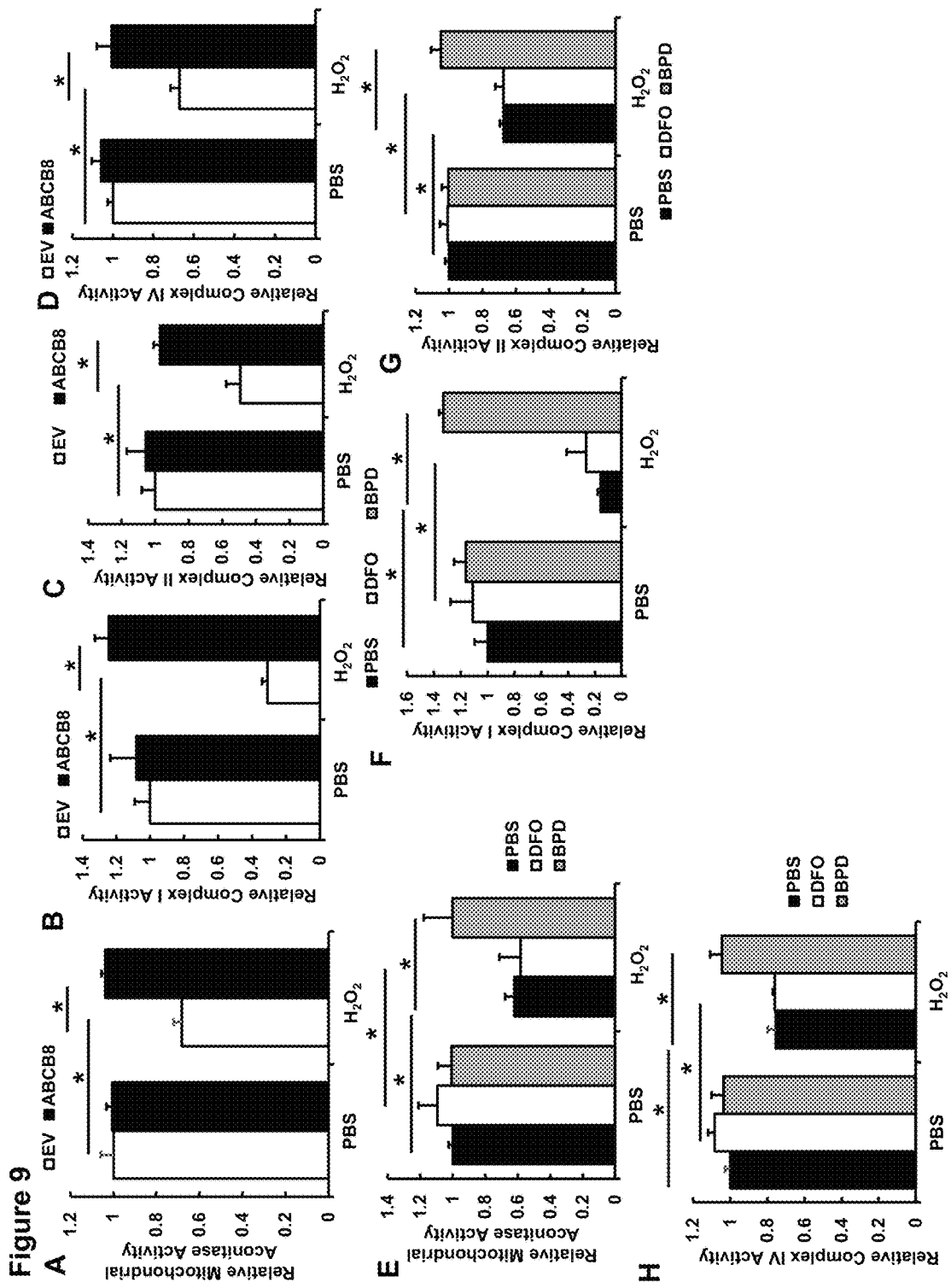
FIG. 9. Modulation of mitochondrial iron preserves the activity of mitochondrial complexes after oxidative stress. A. Mitochondrial aconitase activity in H9c2 cells with or without ABCB8 overexpression and treated with or without $H_2O_2$. N=8 for each group. * P<0.05. B. Complex I activity in H9c2 cells with or without ABCB8 overexpression and treated with or without $H_2O_2$. N=6 for each group. * P<0.05. C. Complex II activity in H9c2 cells with or without ABCB8 overexpression and treated with or without $H_2O_2$. N=6 for each group. * P<0.05. D. Complex IV activity in H9c2 cells with or without ABCB8 overexpression and treated with or without $H_2O_2$. N=6 for each group. * P<0.05. E. Mitochondrial aconitase activity in H9c2 cells treated with indicated iron chelators with or without $H_2O_2$. N=6-8 in each group. * P<0.05. F. Complex I activity in H9c2 cells treated with indicated iron chelators with or without $H_2O_2$. N=6 for each group. * P<0.05. G. Complex II activity in H9c2 cells treated with indicated iron chelators with or without $H_2O_2$. N=6 for each group. * P<0.05. H. Complex IV activity in H9c2 cells treated with indicated iron chelators with or without $H_2O_2$. N=6 for each group. * P<0.05.

Although iron can catalyze ROS production through the Fenton reaction, it is not known whether iron accumulation can also affect mitochondrial respiratory chain complexes (which are the major sources of ROS production in mitochondria (Murphy, 2009; Schieber & Chandel, 2014)), and increase the cellular ROS derived from these structures. To determine whether changes in mitochondrial iron have any effect on mitochondrial complex I and complex III ROS production, we first modulated mitochondrial iron through overexpression or downregulation of ABCB8 in H9c2 cells, followed by measurement of ROS production at baseline. ROS production through complex I was measured in the presence of its substrates malate/pyruvate, while ROS production through complex III was assessed using succinate, the substrate for complex II which directly feeds complex III. Maximal ROS production was measured in the presence of rotenone (for complex I) and antimycin A (for complex III). ABCB8 overexpression was confirmed by western blotting (FIG. 8A). We did not observe any changes in baseline or maximal complex I and complex III ROS production with either downregulation (FIG. 8B-C) or overexpression of ABCB8 (FIG. 8D-E), suggesting that changes in baseline mitochondrial iron do not influence the intrinsic ability of mitochondrial complexes to produce ROS.

Since iron can catalyze the formation of hydroxyl free radicals from hydrogen peroxide and cause cellular damage, we then studied whether modulation of mitochondrial iron influences ROS production and mitochondrial membrane potential in vitro after injury. Mitochondrial ROS, measured by mitoSox, was increased in H9c2 cells after hydrogen peroxide treatment (FIG. 8F). The increase in mitochondrial ROS was significantly attenuated in cells with BPD pretreatment, while DFO pretreatment had no effects. Although this experiment does not directly measure the production of the hydroxyl free radicals, it provides a measure of overall mitochondrial ROS levels after $H_2O_2$ injury. Additionally, while chelator treatment did not have significant effects on mitochondrial membrane potential at baseline, BPD prevented the significant decrease of mitochondrial membrane potential after oxidative stress (FIG. 8G). Thus, our finding is consistent with our hypothesis that lower mitochondrial iron at baseline is associated with less mitochondrial ROS and cellular damage after injury.

To investigate the effects of modulating mitochondrial iron levels on ROS production in vivo after injury, we measured lipid peroxidation products in chelator-treated ABCB8 KO mice and in ABCB8 transgenic mice that had undergone I/R. While ABCB8 KO mice had significantly higher levels of lipid peroxidation products, BPD treatment attenuated the increase (FIG. 8H). Similarly, I/R injury in NTG mice resulted in a higher level of lipid peroxidation products, but the increase was attenuated with ABCB8 overexpression (FIG. 8I). The results indicate that mitochondrial iron modulation has an effect on ROS production during cardiac injury.

Since increased mitochondrial ROS can inhibit mitochondrial TCA cycle enzymes and respiratory chain complexes, we measured the enzymatic activity of mitochondrial aconitase, complex I, II and IV. Mitochondrial aconitase has a labile Fe/S cluster and is prone to oxidative damage (Vasquez-Vivar et al., 2000). Similarly, a decrease in the activity of complex I, II, and IV after oxidative damage has been described previously (Long et al., 2004; Moser et al., 2009; Wu et al., 2010). While ABCB8 overexpression did not cause changes in any of the enzyme activities, it prevented the decrease in mitochondrial aconitase, complex I, II and IV activity after $H_2O_2$ challenge (FIG. 9A-D) Similarly, while iron chelator treatment did not cause any difference in the activity of these enzymes, BPD pre-treatment protected the activities of mitochondrial aconitase, complex I, II and IV after $H_2O_2$ treatment. On the other hand, DFO pre-treatment did not confer any protection (FIG. 9E-H). These findings suggest that preventing ROS production due to mitochondrial iron accumulation during cardiac injury is one of the major mechanisms by which modulation of baseline mitochondrial iron levels is protective.

Changes in Mitochondrial Iron are not Associated with Alterations of Mitochondrial Biogenesis or NOS Expression.

Figure 16:
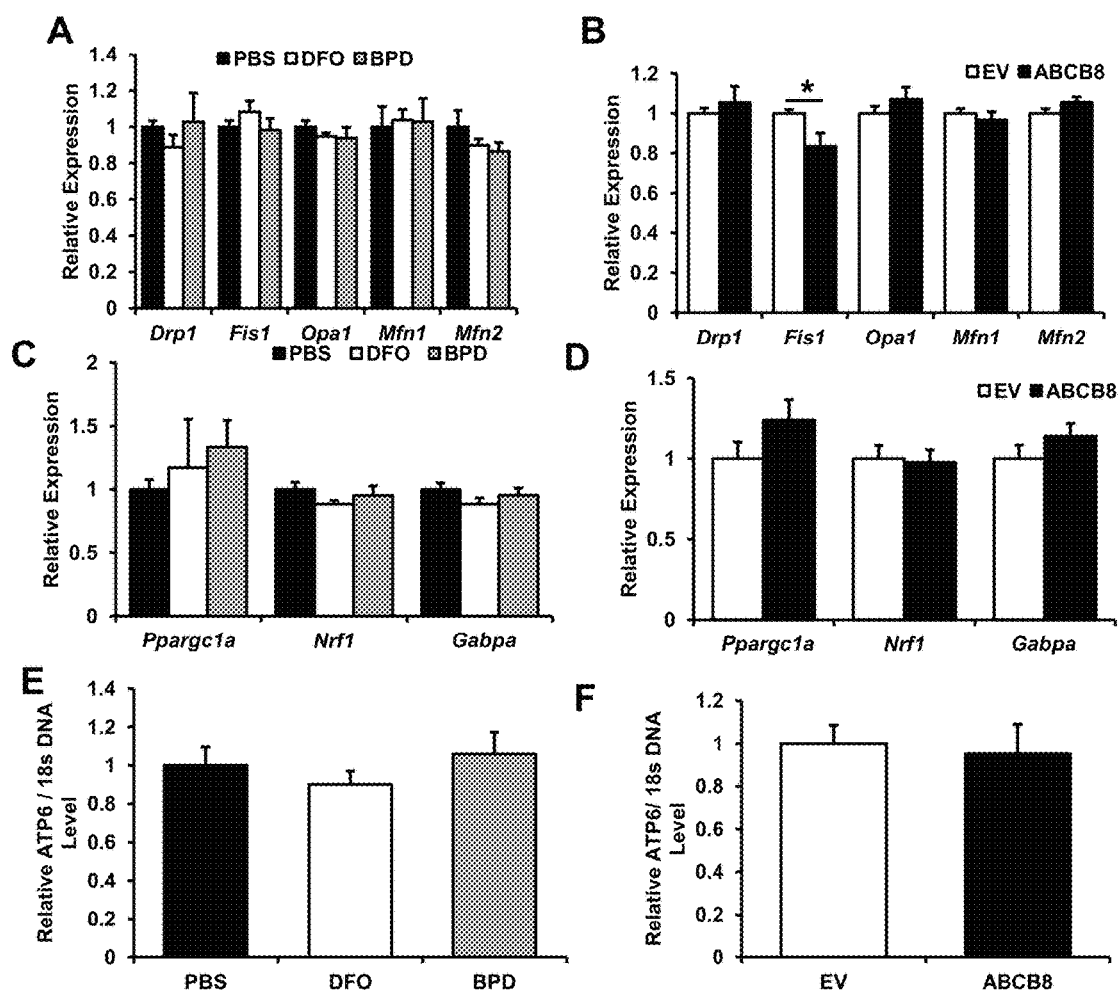
FIG. 16. Effects of mitochondrial iron modulation on mitochondrial biogenesis or dynamics in vitro. A. Expression of genes associated with mitochondrial dynamics in H9c2 cells treated with indicated iron chelator. N=5-6 in each group. B. Expression of genes associated with mitochondrial dynamics in H9c2 cells with ABCB8 overexpression. EV=empty vector. N=5-6 in each group. * P<0.05. C. Expression of genes associated with mitochondrial biogenesis in H9c2 cells treated with indicated iron chelator. N=5-6 in each group. D. Expression of genes associated with mitochondrial biogenesis in H9c2 cells with ABCB8 overexpression. N=5-6 in each group. E. Mitochondrial DNA content in H9c2 cells treated with indicated iron chelator. N=5-6 in each group. F. Mitochondrial DNA content in H9c2 cells with ABCB8 overexpression. N=5-6 in each group.
Figure 17:
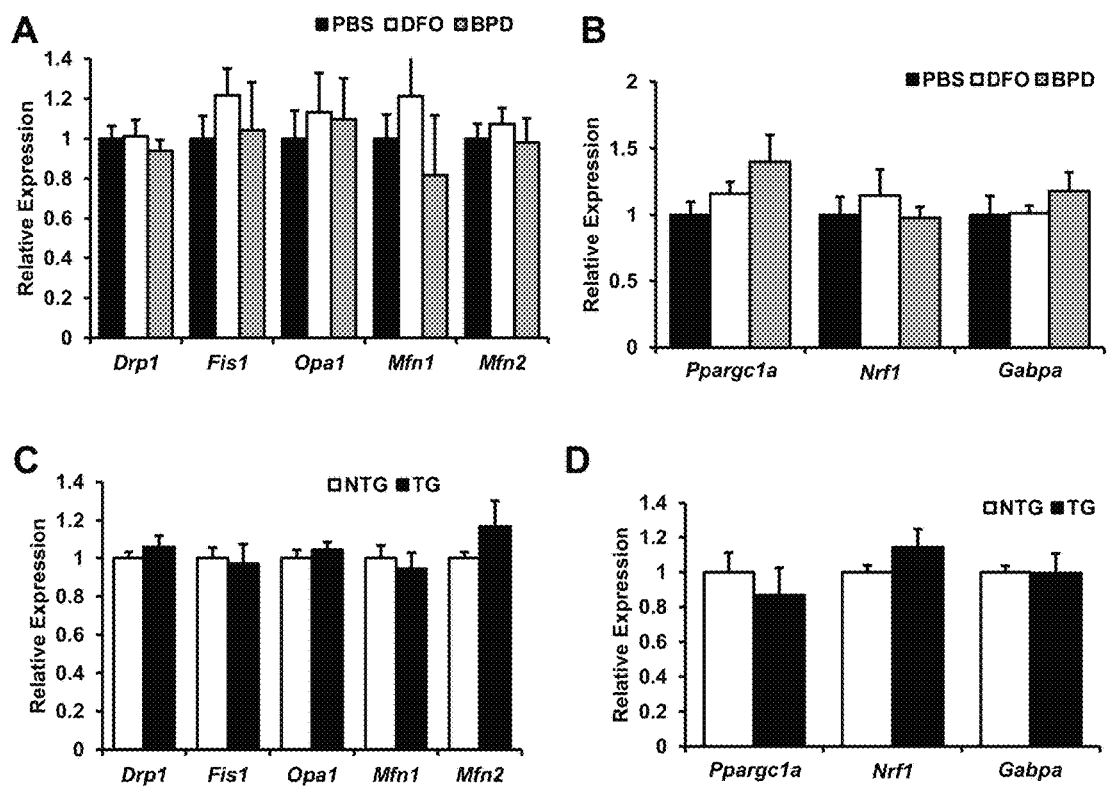
FIG. 17. Effects of mitochondrial iron modulation on mitochondrial biogenesis and dynamics in wild-type mice with chelator treatment and ABCB8 TG mice. A. Expression of genes associated with mitochondrial dynamics in wild-type mice treated with indicated iron chelator. N=5 in each group. B. Expression of genes associated with mitochondrial biogenesis in wild-type mice treated with indicated iron chelator. N=5 in each group. C. Expression of genes associated with mitochondrial dynamics in ABCB8 TG mice. N=6 in each group. D. Expression of genes associated with mitochondrial biogenesis in ABCB8 TG mice. N=6 in each group.

Mitochondrial dynamics have been shown to be associated with mitochondrial ROS production (Jheng et al., 2012; Pletjushkina et al., 2006), and the mitochondrial fission protein dynamin related protein 1 (Drp1) has been linked to apoptosis (Frank et al., 2001). To assess the role of mitochondrial dynamics in the observed protective effects of mitochondrial iron modulation, we measured the expression of genes involved in mitochondrial dynamics in H9c2 cells with ABCB8 overexpression or after treatment with iron chelators. No difference in the gene expression of mitochondrial fusion proteins (optic atrophy 1 (Opa1), mitofusin 1 (Mfn1), and mitofusin 2 (Mfn2)) and fission proteins (fission, mitochondrial 1 (Fis1), and Drp1) was observed in either groups, except for a decrease of Fis1 seen in ABCB8 overexpressing H9c2 cells (FIG. 16A-B). We also measured expression of genes associated with mitochondrial biogenesis and mitochondrial DNA content in these groups and found no difference (FIG. 16C-F). Additionally, the expression of genes involved in mitochondrial biogenesis and mitochondrial dynamics were not altered by pharmacological or genetic modulation of mitochondrial iron in mice (FIG. 17).

Figure 18:
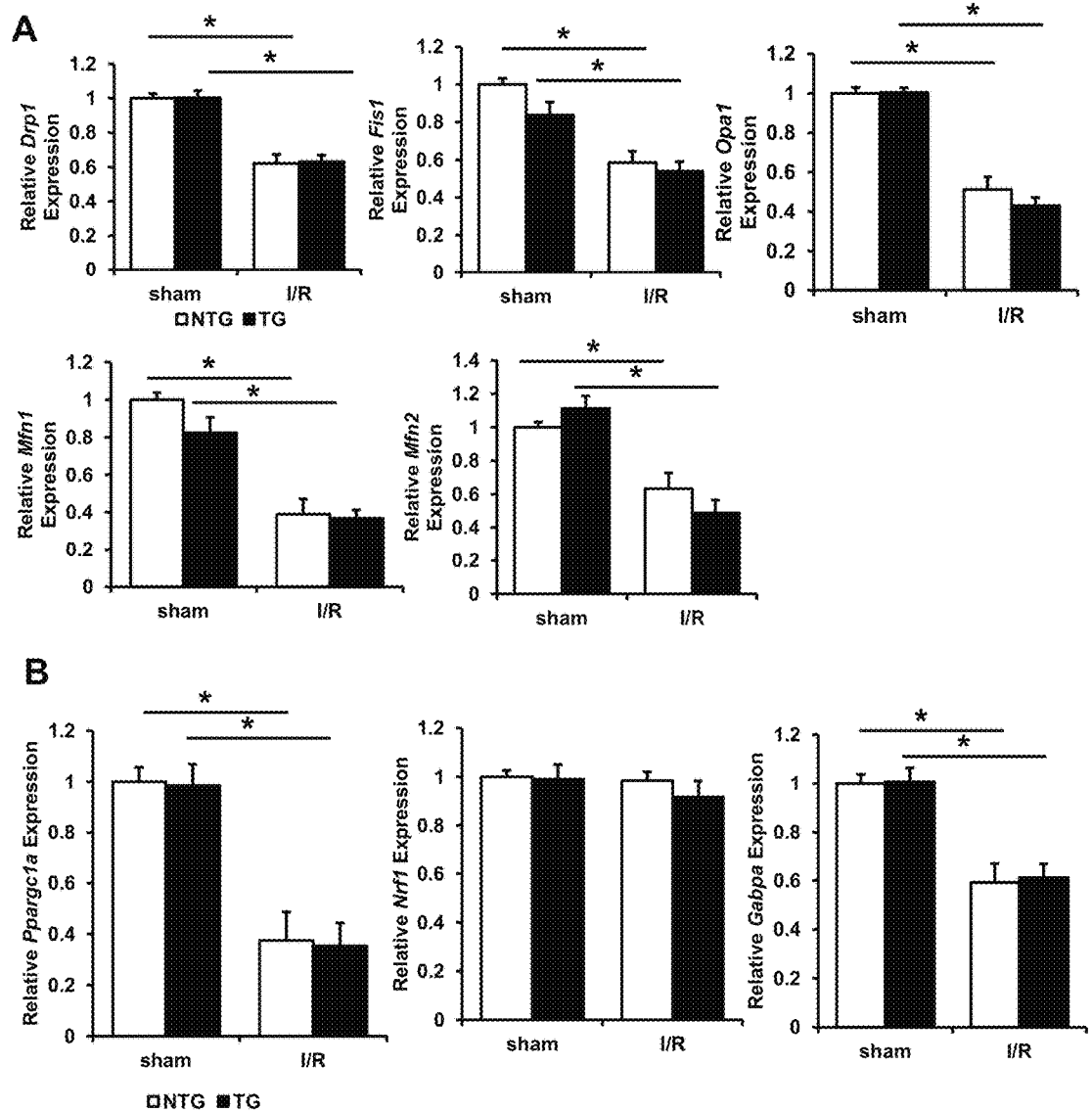
FIG. 18. Effects of mitochondrial iron modulation on mitochondrial biogenesis and dynamics after I/R in vivo. A. Expression of genes associated with mitochondrial dynamics in ABCB8 TG mice subjected to the indicated procedure. N=10-12 in each group. * P<0.05. B. Expression of genes associated with mitochondrial biogenesis in ABCB8 TG mice subjected to the indicated procedure. N=10-12 in each group. * P<0.05

We also evaluated the expression of genes involved in mitochondrial biogenesis and mitochondrial dynamics in NTG and ABCB8 TG mice 2 day after I/R. mRNA levels of genes associated with mitochondrial biogenesis and mitochondrial dynamics were reduced to the same degree in NTG and ABCB8 TG mice in response to I/R (with the exception of nuclear respiratory factor 1, whose expression was not altered by I/R in either group) (FIG. 18). Our observed changes of gene expression after I/R are consistent with published gene microarray datasets (GEO Accession number: GSE61592, GSE4105) (Roy et al., 2006). Taken together, our results indicate that modulation of mitochondrial iron has no effect on mitochondrial biogenesis or dynamics both at baseline and after I/R.

Figure 19:
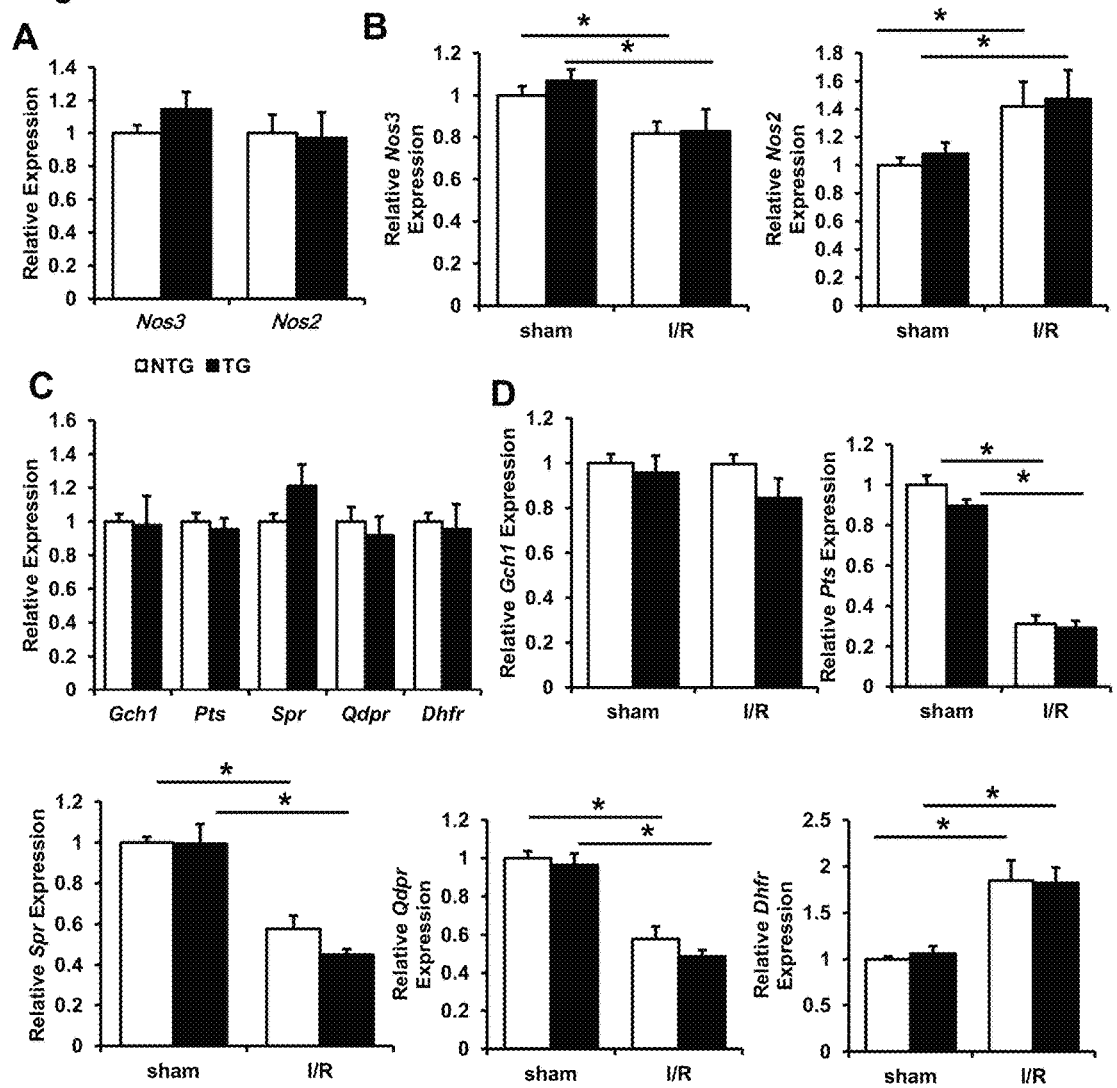
FIG. 19. Effects of mitochondrial iron modulation on the expression of NOS proteins, and genes involved in BH4 biosynthesis both at baseline and after I/R. A. Expression of NOS in ABCB8 TG mice at baseline. N=6 in each group. B. Expression of NOS in ABCB8 TG mice 2 day after I/R. N=10-12 in each group. * P<0.05. C. Expression of genes involved in BH4 biosynthesis in ABCB8 TG mice at baseline. N=6 in each group. D. Expression of genes involved in BH4 biosynthesis in ABCB8 TG 2 day after I/R. N=10-12 in each group. * P<0.05

Nitric oxide synthase (NOS) has also been implicated in I/R injury (Davidson & Duchen, 2006). Therefore, we examined the expression of NOS genes both at baseline and after I/R in NTG and ABCB8 TG mice. Our results showed no difference in the expression of Nos3 and Nos2 (encoding eNOS and iNOS, respectively) between TG and NTG mice both at baseline and 2 days after sham or I/R operation (FIG. 19A-B). Since NOS uncoupling secondary to the loss of its cofactor, BH4, can result in ROS production (Verhaar et al., 2004), we also measured the expression of genes in the BH4 synthesis pathway, and found no difference between NTG and ABCB8 TG mice at baseline, or 2 days after sham or I/R procedures (FIG. 19C-D). Collectively, our data indicate that a decrease in mitochondrial iron has no effect on the expression of NOS proteins or their uncoupling. Therefore, the protective effects of mitochondrial iron modulation cannot be attributed to a NOS-mediated mechanism.

Discussion

The association between changes in iron and ischemic injury has been demonstrated in various organ systems (Comporti et al., 2002; Coudray et al., 1994; Kaushal & Shah, 2014; Zhao et al., 1997). These observations gave rise to the hypothesis that modulation of iron is protective against ischemic damage. However, the effects of iron chelation are very inconsistent among different studies Importantly, none of the previous studies had focused on the role of iron in specific intracellular locations. Based on our observation that mitochondrial iron is significantly increased in mice after I/R, in cells treated with $H_2O_2$, and in human patients with ISCM, we hypothesized that a specific reduction in mitochondrial iron would offer protection against cardiac injury. We further hypothesized that the discrepancies observed between the efficacies of iron chelators in earlier studies could be due to intrinsic differences in their ability to penetrate the mitochondria. Here, we show that a decrease in mitochondrial iron at baseline in vivo using either genetic or pharmacological approaches is protective against I/R damage. We further demonstrate that preventing mitochondrial iron accumulation can be a viable therapeutic approach against the deterioration of cardiac function in a mouse model of genetic mitochondrial iron overload in the heart. The protective effects seen in both models can be attributed to a reduction in ROS production during injury. Thus, our studies highlight the importance of mitochondrial iron in I/R damage.

Our findings are consistent with a recently published randomized clinical trial showing that chelation therapy using EDTA in patients with myocardial infarction reduced adverse cardiovascular outcomes (Lamas et al., 2013), as well as other studies suggesting therapeutic benefits of iron chelation in heart disease (Badylak et al., 1987; Chopra et al., 1992; Kobayashi et al., 1991; Lesnefsky et al., 1990b; Nicholson et al., 1997; Ramesh Reddy et al., 1989; Williams et al., 1991). However, a controversy in this field pertains to the use of iron chelation or iron supplementation as a therapy for patients with heart failure. Other recent clinical trials suggest that patients with heart failure and iron deficiency may benefit from iron supplementation (Anker et al., 2009; Ponikowski et al., 2014), and there are currently attempts to initiate a phase III clinical study to assess the effects of intravenous iron infusion in heart failure. The discrepancy between this and our studies can be explained by the discordance between systemic iron status and cellular iron status. While cardiac mitochondrial iron overload occurs in heart failure patients (Khechaduri et al., 2013), they may be simultaneously iron deficient at the systemic level. Reversal of iron deficiency through intravenous iron may correct many patients' symptoms due to its effect on hematopoiesis and account for the improvement in patients' functional capacities. However, changes in systemic iron status are physiologically distinct from disturbances in subcellular iron homeostasis, and mitochondrial iron overload in the heart would persist in these patients. Based on our data, decreasing iron in this compartment would have beneficial effects on cardiac disease progression.

Mitochondria contain 10-20 µM of labile iron, but the exact concentration can vary from organ to organ (Petrat et al., 2002a; Rauen et al., 2007). While the level of "free" iron (not bound to any ligands) in the mitochondria is not readily determined, it is expected to be low given the tight regulation of cellular iron flux and storage. However, ROS are known to damage iron-containing molecules, especially Fe/S clusters, and free-up incorporated iron (Brazzolotto et al., 1999; Cantu et al., 2009; Flint et al., 1993; Jang & Imlay, 2007). Therefore, in I/R, in which ROS levels are increased, the amount of free iron in the mitochondria may be higher than basal conditions. Increased labile iron may also disrupt mitochondrial iron homeostasis, resulting in the increased mitochondrial iron observed in the acute phase of I/R injury in our in vivo studies. Furthermore, increased lysosomal delivery of iron to mitochondria during ischemia can also lead to increased mitochondrial iron levels (Zhang & Lemasters, 2013). It is possible that all of these mechanisms contribute to the increase in mitochondrial iron in mouse hearts after I/R. The increased iron level in turn further augments ROS production, which can inhibit mitochondrial aconitase, complex I and complex II activity (as observed in ours and other studies (Chen & Zweier, 2014)), and can cause cytochrome C release secondary to AMPK activation (Dixon & Stockwell, 2014). Therefore, a decrease in baseline mitochondrial iron could lead to less "free" and total iron during oxidative stress, thereby reducing iron-catalyzed ROS production and cell death.

Earlier studies have suggested that DFO might protect radiation-mediated or low-dose $H_2O_2$-induced cell death through a lysosomal-iron dependent mechanism (Persson et al., 2005; Yu et al., 2003). Although lysosomal iron may contribute to the I/R injury, damage to mitochondrial respiratory chain activity, mitochondrial membrane lipids and mitochondrial DNA from mitochondria-derived ROS are likely to be more important during tissue I/R. As DFO predominantly exerts its effect through iron-binding in the extracellular space and endosome (Doulias et al., 2003; Lloyd et al., 1991), the inability to modulate mitochondrial iron can explain the lack of efficacy of DFO in our in vivo experiments, which is also consistent with some other large animal studies as well as a recent clinical trial (Chan et al., 2012; Chopra et al., 1992; Kobayashi et al., 1991; Lesnefsky et al., 1990b; Ramesh Reddy et al., 1989). In contrast, the ability of BPD to penetrate into subcellular compartments (Demougeot et al., 2004) may explain its protective effects in our in vitro and in vivo models. While iron chelators also have systemic effects and can modulate mitochondrial iron in other organs in addition to the heart, our genetic model specifically lowers mitochondrial iron in the cardiomyocyte. Therefore, the results from these two models argue that cardiac mitochondrial iron plays a causative role in I/R damage. These findings, combined with our observation of increased mitochondrial iron in I/R, underscore the significance of targeting mitochondrial iron in developing future therapies.

Our transgenic model of cardiac-specific ABCB8 overexpression displayed lower levels of mitochondrial iron while cytosolic iron remained similar. The lower amount of mitochondrial iron can be due to increased iron export, as seen in other studies (Ichikawa et al., 2012). Since the majority of intracellular iron is stored in ferritin molecules in the cytoplasm, mitochondrial iron only represents a small fraction of the total cellular iron. This is supported by experiments in which cells are incubated with a radioactive iron chaser and the majority of radioactivity concentrates in the cytoplasm. Therefore, the approximately 20% decrease in mitochondrial iron seen in our transgenic model might not significantly affect the total cellular iron level.

Although targeting whole-cell ROS using antioxidants did not show benefits in different disease settings, including cardiovascular disease and cancer (Fortmann et al., 2013; Jha et al., 1995; Steinhubl, 2008), recent animal studies and human trials using mitochondria-targeted antioxidants have offered promising results (Adlam et al., 2005; Dai et al., 2011; Gane et al., 2010; Neuzil et al., 2007; Xu et al., 2008). Preclinical studies also highlighted the involvement of Complex III-mediated ROS production during tissue ischemia (Lesnefsky & Hoppel, 2003). These findings indicate that targeting antioxidants to the proper site of ROS production is critical. While our studies suggest that modulation of mitochondrial iron does not have an effect on baseline ROS production, the excess free iron during I/R can convert the ROS from mitochondrial complexes and generate more damage, which would explain the difference in lipid peroxidation products in our in vivo system. Our studies emphasize the importance of targeting mitochondrial iron (which ultimately results in a reduction in mitochondrial ROS) during I/R injury, and the design of future therapies should take into consideration the subcellular specificity of the intervention.

In summary, we demonstrated that mitochondrial iron is a key player in ischemic damage to the heart. Genetic and pharmacological approaches lowering mitochondrial iron at baseline led to reduced cardiac damage from I/R. We also showed that mitochondrial iron plays a causative role in the development of cardiomyopathy in a genetic model of cardiac mitochondrial iron accumulation. Lastly, the protective effect of modulating baseline mitochondrial iron is at least partially through a reduction in mitochondrial ROS production.

Materials and Methods

Human Heart Failure Tissue Samples.

Non-failing and ischemic cardiomyopathy cardiac tissue samples were obtained from the Human Heart Tissue Collection at the Cleveland Clinic. Informed consent was obtained from all the transplant patients and from the families of the organ donors before tissue collection. Protocols for tissue procurement were approved by the Institutional Review Board of the Cleveland Clinic (Cleveland, Ohio, USA), which is AAHRPP accredited.

Mouse Model.

Cardiomyocyte-specific ABCB8 transgenic mice were generated as described previously (Ichikawa et al., 2014) and backcrossed for at least 8 generations. Mice with both alleles of ABCB8 floxed (ABCB8f/f) were crossed to α-MHC MER-Cre-MER mice, and the first generation is back-crossed with ABCB8f/f mice to generate ABCB8f/f mice with or without α-MHC MER-Cre-MER transgene. Tamoxifen-induced Cre translocation and deletion of ABCB8 in the heart was achieved using a previously described protocol (Ichikawa et al., 2012). All animal studies were approved by the Institutional Animal Care and Use Committee at Northwestern University and were performed in accordance with guidelines from the National Institutes of Health.

Iron Chelator Treatment.

Mice were treated with 80 mg/kg BPD (Sigma) in normal saline solution daily or 50 mg/kg DFO (Sigma) in normal saline every other day via intraperitoneal injection. The dose of BPD was chosen based on its ability to modulate cardiac mitochondrial iron, and the dose of DFO was chosen according to previously published studies (Ichikawa et al., 2014). BPD was prepared as a 400 mg/ml stock solution in ethanol and diluted 1:100 in normal saline to working concentration. DFO was prepared as a 250 mg/ml stock in water and diluted 1:100 in normal saline to working concentration.

Ischemia-Reperfusion.

The procedure was performed as described previously (Wu et al., 2011).

Echocardiography.

Parasternal short- and long-axis views of the heart were obtained using a Vevo 770 high-resolution imaging system with a 30 MHz scan head. 2D and M-mode images were obtained and analyzed. Ejection fraction was calculated from M mode image using Teichholtz equation, and fractional shortening was directly calculated from end-systolic and end-diastolic chamber size from M-mode images.

Histochemical Analysis.

At the time of tissue harvest, heart was excised and rinsed in phosphate buffered saline to remove excess blood on tissue and in ventricles. Hearts were then submerged into OTC compound and frozen in liquid nitrogen. For hearts with I/R injury, sections were collected 500 µm below suture line to capture the injured region. Sections were stained with hematoxylin and eosin for evaluation of general cardiac morphology and tissue organization. Masson Trichrome staining were used to visualize cardiac fibrosis. Fibrosis was quantified from low power microscope images by dividing the arc length of fibrotic scar to the circumference of left ventricle.

For confocal microscopy, frozen sections were fixed in cold acetone. Nonspecific antigen binding was blocked by incubating sections with 5% donkey serum prior to incubating sections with antibody against ABCB8 and COX4 (Abcam) in 4 degree overnight. Species-specific secondary antibody with different fluorophore (Jackson Immunochem) were used to visualize the antigen, and nucleus were counterstained with TO-PRO-3 stain. Images were acquired on a Zeiss LSM510 confocal microscope.

Cell Culture.

H9c2 cardiomyoblasts were cultured in DMEM (ATCC) supplemented with 10% FBS (Thermo) and Penicillin/Streptomycin (Cellgro). HEK293T cells were cultured in MEM (Cellgro) supplemented with 10% FBS, sodium pyruvate (Cellgro) and Penicillin/Streptomycin. Unless otherwise specified, cells were treated with 200 µM of DFO or 100 µM of BPD for two hours when indicated prior to addition of 600 µM of $H_2O_2$ when indicated for 6 hours. RNA isolation and qRT-PCR RNA was isolated using RNA-STAT60 (Tel-Test) according to the manufacturer's instructions, and subjected to DNAse I (Ambion) digestion to remove residual DNA. Purified RNA was then reverse transcribed with Random Hexamer and Oligo dT(16) (Applied Biosystems) and amplified on a 7500 Fast Real-Time PCR system using Fast SYBR Green PCR Master Mix (Applied Biosystems). mRNA levels were calculated based on the difference of threshold Ct values in target gene and average Ct values of 18s, Actb, B2m, and Hprt in the same sample.

Isolation of Mitochondria and Nuclei.

Mitochondria from tissues and cells were isolated via differential centrifugation using the Mitochondria Isolation Kit for Tissue and Mitochondria Isolation Kit for Mammalian Cells (Pierce), respectively. Nuclei were isolated using NE-PER Nuclear and Cytoplasmic Extraction Reagents (Pierce).

Measurement of Iron.

Tissue iron was measured colorimetrically by the formation of a complex with bathophenanthroline disulfonate or ferene-S as described previously (Ichikawa et al., 2012; Khechaduri et al., 2013). For qualitative measurement of mitochondrial labile iron, cells were stained with Rhodamine B-[1,10-phenanthrolin-5-yl)-aminocarbonyl]benzyl ester (RPA) (Squarix) and mitoTracker Green (Invitrogen). Images were obtained on a Zeiss AxioObserver.Z1 microscope. Quantitative measurement of labile iron was done according to previously described methods (Cabantchik et al., 1996; Petrat et al., 2002b). Briefly, cells were stained with RPA and mitoTracker Green for mitochondrial labile iron measurement and calcein (Invitrogen) and Hoechst 33342 (Invitrogen) for cytosolic labile iron measurement. Fluorescence intensity was measured using Gemini XS plate reader (Molecular Device) with following excitation emission setting: ex/em 490 nm/520 nm for mitoTracker Green and calcein, 564 nm/601 nm for RPA, and 350 nm/461 nm for Hoechst 33342. After initial measurement, 2 mM of PIH (Abcam) was added to each well and fluorescence signal was measured again. The difference of fluorescence intensity before and after PIH addition were used to calculate the concentration of iron-binding calcein or RPA based on a standard curve generated using fixed concentration of calcein or RPA. To account for difference in cell number due to plating or treatment with iron chelator and/or $H_2O_2$, the concentration of iron-binding RPA and calcein were normalized to mitoTracker Green and Hoechst 33342 signal of the same well, respectively.

For nuclear and cytosolic iron, cells were loaded with 280 nM of $^{55}$Fe-NTA. Excess $^{55}$Fe-NTA was washed off with cold PBS containing 200 µM DFO prior to chelator treatment. The nuclear and cytosolic fractions were isolated using NE-PER Nuclear and Cytoplasmic Extraction Reagents (Pierce) and the radioactivity was quantified with liquid scintillation.

Measurement of Lipid Peroxidation Products.

MDA and HAE in tissue samples were analyzed using the LPO microplate-based assay kit (Oxford Biochemical Research) according to the manufacturer's instructions.

Cell Death Studies.

For in vitro studies, cells were resuspended in 1×Annexin V buffer (BD) and then stained with Alexa Fluor 350 conjugated Annexin V (Life Technology) and propidium iodide (Sigma) according to the manufacturer's instructions and analyzed on a LSRII flow cytometer (BD).

For measuring apoptosis in tissue sections, sections were stained using an in situ cell death detection kit (Roche) according to the manufacturer's instructions and then counterstained with DAPI (Sigma) and Cy5-Phalloidin (Molecular Probes). Images were obtained on a Zeiss AxioObserver.Z1 microscope.

Overexpression and Downregulation of ABCB8.

For knockdown studies, pooled ABCB8 siRNA or control siRNA (Qiagen) were transfected into H9c2 cells using Dharmafect I reagent (GE Healthcare) for 72 hours according to manufacturer's protocol. The effectiveness of this siRNA was verified before (Ichikawa et al., 2012). ABCB8 overexpression was achieved by cloning the ABCB8 coding sequence into the pHIV-eGFP vector (Addgene). Sequences were verified through direct sequencing. Virus was generated by transfecting HEK293T cells with packaging plasmid and viral construct using calcium phosphate transfection. Equal titers of ABCB8 or empty vector virus were used to infect H9c2 cells for 72 hours. Overexpression was verified with western blotting.

Measurement of Mitochondrial ROS Production and Mitochondrial ROS Levels.

Mitochondria were isolated as described before, and resuspended in buffer containing 220 mM mannitol, 75 mM sucrose, 20 mM HEPEs (pH 7.4), 0.5 mM EDTA, 0.1 mM ATP, 0.5 mM magnesium acetate. Mitochondria were fueled with 10 mM of succinate or 3 mM sodium pyruvate and 3 mM sodium malate. ROS production was measured by Amplex Ultra Red (Life Technologies) according to the manufacturer's instructions in the presence of 2 U/ml HRP and 200 U/ml SOD. Rotenone (complex I inhibitor, Sigma) and antimycin A (complex III inhibitor, Sigma) were added when indicated.

Mitochondrial ROS levels in intact cells were quantified using MitoSox Red (Life Technologies). Briefly, cells were loaded with MitoSox to stain for mitochondrial ROS and Hoechst 33342 for nuclei counter stain. Images were obtained on a Zeiss AxioObserver.Z1 microscope and analyzed with ImageJ software (NIH). MitoSox signal in the nuclei was subtracted to exclude localization of the dye to the nuclei.

Western Blotting.

Whole cell lysate or subcellular fractions were loaded onto 4-12% Bis-Tris acrylamide gel (Life Technology) and transferred to nitrocellulose membrane (GE Life Science). Membrane was incubated with primary antibody against ABCB8 (Ardehali et al., 2005), tubulin, GAPDH (Abcam), SDH70 kDa (Life Technologies), or lamin A/C (Cell Signaling) overnight in TBS with 0.05% Tween 20 and 5% milk. The membrane was then hybridized with horse-radish peroxidase conjugated secondary antibody against rabbit or mouse (Jackson Immunochem), and the signal was visualized using Supersignal West Pico Substrate (Life Technologies).

Mitochondrial Enzyme and Complex Activities Measurement.

Mitochondria were isolated from cells as described above. Mitochondrial complex I, II and IV activity was measured as described previously (Spinazzi et al., 2012). Aconitase activity was measured using Aconitase Activity Microplate Assay Kit (Abcam). Citrate synthase activity was measured from the same sample using Citrate Synthase Activity Kit (BioVision) and was used to normalize the mitochondrial complex activity.

Mitochondrial DNA Content Measurement.

Genomic and mitochondrial DNA from H9c2 cells were isolated using GeneJet DNA Isolation Kit (Thermo Scientific) according to manufacturer's instruction. The isolated DNA were diluted 1:10 and used as template for amplifying regions of ATP6 (mitochondrial DNA) and 18s (nuclear DNA) sequences. PCR were carried out on a 7500 Fast Real-Time PCR system using Fast SYBR Green PCR Master Mix (Applied Biosystems). The abundance of mitochondrial DNA was calculated based on difference of threshold Ct values between ATP6 and 18s.

Mitochondrial Membrane Potential Measurement.

Cells were stained with 5 nM of TMRE (Life Technology) and counter stained with Hoechst 33342. Images were obtained on a Zeiss AxioObserver.Z1 microscope and analyzed with ImageJ software (NIH).

Statistical Analysis.

Data are expressed as mean±SEM. Statistical significance was assessed with ANOVA, and post-hoc Tukey test was performed when appropriate; a p value of less than 0.05 was considered statistically significant.

REFERENCES

Adlam V J, Harrison J C, Porteous C M, James A M, Smith R A, Murphy M P, Sammut I A (2005) Targeting an antioxidant to mitochondria decreases cardiac ischemia-reperfusion injury. FASEB journal: official publication of the Federation of American Societies for Experimental Biology 19: 1088-1095.

Aigner E, Theurl I, Theurl M, Lederer D, Haufe H, Dietze O, Strasser M, Datz C, Weiss G (2008) Pathways underlying iron accumulation in human nonalcoholic fatty liver disease. The American Journal of Clinical Nutrition 87: 1374-1383.

Anker S D, Comin Colet J, Filippatos G, Willenheimer R, Dickstein K, Drexler H, Luscher T F, Bart B, Banasiak W, Niegowska J et al (2009) Ferric Carboxymaltose in Patients with Heart Failure and Iron Deficiency. New England Journal of Medicine 361: 2436-2448.

Ardehali H, O'Rourke B, Marban E (2005) Cardioprotective Role of the Mitochondrial ATP-Binding Cassette Protein 1. Circulation Research 97: 740-742 Badylak S F, Simmons A, Turek J, Babbs C F (1987) Protection from reperfusion injury in the isolated rat heart by postischaemic deferoxamine and oxypurinol administration. Cardiovascular Research 21: 500-506.

Braunwald E (2013) Heart Failure. JACC: Heart Failure 1: 1-20.

Brazzolotto X, Gaillard J, Pantopoulos K, Hentze M W, Moulis J-M (1999) Human Cytoplasmic Aconitase (Iron Regulatory Protein 1) Is Converted into Its [3Fe-4S] Form by Hydrogen Peroxide in Vitro but Is Not Activated for Iron-responsive Element Binding. Journal of Biological Chemistry 274: 21625-21630.

Cabantchik Z I, Glickstein H, Milgram P, Breuer W (1996) A fluorescence assay for assessing chelation of intracellular iron in a membrane model system and in mammalian cells. Analytical biochemistry 233: 221-227.

Cantu D, Schaack J, Patel M (2009) Oxidative Inactivation of Mitochondrial Aconitase Results in Iron and $H_2O_2$-Mediated Neurotoxicity in Rat Primary Mesencephalic Cultures. PLoS ONE 4: e7095.

Chan W, Taylor A J, Ellims A H, Lefkovits L, Wong C, Kingwell B A, Natoli A, Croft K D, Mori T, Kaye D M et al (2012) Effect of Iron Chelation on Myocardial Infarct Size and Oxidative Stress in S T-Elevation. Myocardial Infarction. Circulation: Cardiovascular Interventions 5: 270-278.

Chatziathanasiou G N, Nikas Dn Fau—Katsouras C S, Katsouras Cs Fau—Kazakos N D, Kazakos Nd Fau—Bouba V, Bouba V Fau—Vougiouklakis T, Vougiouklakis T Fau—Naka K K, Naka Kk Fau Michalis L K, Michalis L K (2012) Combined intravenous treatment with ascorbic acid and desferrioxamine to reduce myocardial reperfusion injury in an experimental model resembling the clinical setting of primary PCI. Hellenic Journal of Cardiology 2012: 195-204.

Chen Y R, Zweier J L (2014) Cardiac mitochondria and reactive oxygen species generation. Circ Res 114: 524-537.

Chopra K, Singh M Fau—Kaul N, Kaul N Fau—Andrabi K I, Andrabi Ki Fau—Ganguly N K, Ganguly N K (1992) Decrease of myocardial infarct size with desferrioxamine: possible role of oxygen free radicals in its ameliorative effect. Molecular and Cellular Biochemistry 113: 71-76.

Comporti M, Signorini C, Buonocore G, Ciccoli L (2002) Iron release, oxidative stress and erythrocyte ageing. Free radical biology & medicine 32: 568-576.

Coudray C, Pucheu S, Boucher F, Arnaud J, Leiris J, Favier A (1994) Effect of ischemia/reperfusion sequence on cytosolic iron status and its release in the coronary effluent in isolated rat hearts. Biol Trace Elem Res 41: 69-75.

Dai D F, Chen T, Szeto H, Nieves-Cintron M, Kutyavin V, Santana L F, Rabinovitch P S (2011) Mitochondrial targeted antioxidant Peptide ameliorates hypertensive cardiomyopathy. J Am Coll Cardiol 58: 73-82.

Davidson S M, Duchen M R (2006) Effects of NO on mitochondrial function in cardiomyocytes: Pathophysiological relevance. Cardiovascular Research 71: 10-21.

De Domenico I, McVey Ward D, Kaplan J (2008) Regulation of iron acquisition and storage: consequences for iron-linked disorders. Nat Rev Mol Cell Biol 9: 72-81.

de Vries B, Walter S J, von Bonsdorff L, Wolfs T G, van Heurn L W, Parkkinen J, Buurman W A (2004) Reduction of circulating redox-active iron by apotransferrin protects against renal ischemia-reperfusion injury. Transplantation 77: 669-675.

Demougeot C, Van Hoecke M, Bertrand N, Prigent-Tessier A, Mossiat C, Beley A, Marie C (2004) Cytoprotective Efficacy and Mechanisms of the Liposoluble Iron Chelator 2,2'-Dipyridyl in the Rat Photothrombotic Ischemic Stroke Model. Journal of Pharmacology and Experimental Therapeutics 311: 1080-1087.

Dixon S J, Stockwell B R (2014) The role of iron and reactive oxygen species in cell death. Nat Chem Biol 10: 9-17.

Doulias P-T, Christoforidis S, Brunk U T, Galaris D (2003) Endosomal and lysosomal effects of desferrioxamine: protection of HeLa cells from hydrogen peroxide-induced DNA damage and induction of cell-cycle arrest. Free Radical Biology and Medicine 35: 719-728.

Eaton J W, Qian M (2002) Molecular bases of cellular iron toxicity. Free Radical Biology and Medicine 32: 833-840.

Flint D H, Tuminello J F, Emptage M H (1993) The inactivation of Fe—S cluster containing hydro-lyases by superoxide. Journal of Biological Chemistry 268: 22369-22376.

Foo R S Y, Mani K, Kitsis R N (2005) Death begets failure in the heart. The Journal of Clinical Investigation 115: 565-571.

Fortmann S P, Burda B U, Senger C A, Lin J S, Whitlock E P (2013) Vitamin and mineral supplements in the primary prevention of cardiovascular disease and cancer: An updated systematic evidence review for the U.S. Preventive Services Task Force. Ann Intern Med 159: 824-834.

Frank S, Gaume B, Bergmann-Leitner E S, Leitner W W, Robert E G, Catez F, Smith C L, Youle R J (2001) The Role of Dynamin-Related Protein 1, a Mediator of Mitochondrial Fission, in Apoptosis. Developmental Cell 1: 515-525.

Furukawa T, Naitoh Y, Kohno H, Tokunaga R, Taketani S (1992) Iron deprivation decreases ribonucleotide reductase activity and DNA synthesis. Life sciences 50: 2059-2065.

Gane E J, Weilert F, Orr D W, Keogh G F, Gibson M, Lockhart M M, Frampton C M, Taylor K M, Smith R A, Murphy M P (2010) The mitochondria-targeted antioxidant mitoquinone decreases liver damage in a phase I I study of hepatitis C patients. Liver international: official journal of the International Association for the Study of the Liver 30: 1019-1026.

Gao X, Campian J L, Qian M, Sun X-F, Eaton J W (2009) Mitochondrial DNA Damage in Iron Overload. Journal of Biological Chemistry 284: 4767-4775.

Ghio A J (2009) Disruption of iron homeostasis and lung disease. Biochimica et Biophysica Acta (BBA)—General Subjects 1790: 731-739.

Gille G, Reichmann H (2011) Iron-dependent functions of mitochondria.relation to neurodegeneration. J Neural Transm 118: 349-359.

Gomez M, Perez-Gallardo R V, Sanchez L A, Diaz-Perez A L, Cortes-Rojo C, Meza Carmen V, Saavedra-Molina A, Lara-Romero J, Jimenez-Sandoval S, Rodriguez F et al (2014). Malfunctioning of the Iron-Sulfur Cluster Assembly Machinery in Saccharomyces cerevisiae Produces Oxidative Stress via an Iron-Dependent Mechanism, Causing Dysfunction in Respiratory Complexes. PLoS ONE 9: e111585.

Hentze M W, Muckenthaler M U, Galy B, Camaschella C (2010) Two to Tango: Regulation of Mammalian Iron Metabolism. Cell 142: 24-38.

Heron M (2013) Deaths: Leading Causes for 2010. In National Vital Statistics Report. Hyattsville, Md.: National Center for Health Statistics.

Hirst J (2013) Mitochondrial Complex I. Annual Review of Biochemistry 82: 551-575.

Hollenbeck R D, McPherson J A, Mooney M R, Unger B T, Patel N C, McMullan P W, Jr., Hsu C H, Seder D B, Kern K B (2014) Early cardiac catheterization is associated with improved survival in comatose survivors of cardiac arrest without STEMI. Resuscitation 85: 88-95.

Horowitz M P, Greenamyre J T (2010) Mitochondrial iron metabolism and its role in neurodegeneration. Journal of Alzheimer's disease: JAD 20 Suppl 2: S551-568.

Ichikawa Y, Bayeva M, Ghanefar M, Potini V, Sun L, Mutharasan R K, Wu R, Khechaduri A, Jairaj Naik T, Ardehali H (2012) Disruption of ATP-binding cassette B8 in mice leads to cardiomyopathy through a decrease in mitochondrial iron export. Proceedings of the National Academy of Sciences 109: 4152-4157.

Ichikawa Y, Ghanefar M, Bayeva M, Wu R, Khechaduri A, Prasad S V N, Mutharasan R K, Naik T J, Ardehali H (2014) Cardiotoxicity of doxorubicin is mediated through mitochondrial iron accumulation. The Journal of Clinical Investigation 124: 617-630.

Jang S, Imlay J A (2007) Micromolar Intracellular Hydrogen Peroxide Disrupts Metabolism by Damaging Iron-Sulfur Enzymes. Journal of Biological Chemistry 282: 929-937.

Jha P, Rather M, Lonn E, Farkouh M, Yusuf S (1995) The Antioxidant Vitamins and Cardiovascular Disease: A Critical Review of Epidemiologic and Clinical Trial Data. Annals of Internal Medicine 123: 860-872.

Jheng H-F, Tsai P-J, Guo S-M, Kuo L-H, Chang C-S, Su I-J, Chang C-R, Tsai Y-S (2012). Mitochondrial Fission Contributes to Mitochondrial Dysfunction and Insulin Resistance in Skeletal Muscle. Molecular and Cellular Biology 32: 309-319.

Kaushal G P, Shah S V (2014) Challenges and Advances in the Treatment of AKI. Journal of the American Society of Nephrology 25: 877-883.

Khechaduri A, Bayeva M, Chang H-C, Ardehali H (2013) Heme Levels Are Increased in Human Failing Hearts. Journal of the American College of Cardiology 61: 1884-1893.

Kispal G, Sipos K, Lange H, Fekete Z, Bedekovics T, Janaky T, Bassler J, Aguilar Netz D J, Balk J, Rotte C et al (2005) Biogenesis of cytosolic ribosomes requires the essential iron-sulphur protein Rlilp and mitochondria. EMBO J 24: 589-598.

Kobayashi S, Tadokoro H, Wakida Y, Kar S, Nordlander R, Haendchen R V, Corday E (1991). Coronary venous retroinfusion of deferoxamine reduces infarct size in pigs. Journal of the American College of Cardiology 18: 621-627.

Kurz T, Eaton J W, Brunk U T (2010) Redox activity within the lysosomal compartment: implications for aging and apoptosis. Antioxidants & redox signaling 13: 511-523.

Lamas G A, Goertz C, Boineau R, et al. (2013) Effect of disodium edta chelation regimen on cardiovascular events in patients with previous myocardial infarction: The tact randomized trial. JAMA 309: 1241-1250.

Lesnefsky E J, Hedlund B E, Hallaway P E, Horwitz L D (1990a) High-Dose Iron-Chelator Therapy During Reperfusion with Deferoxamine-Hydroxyethyl Starch Conjugate Fails to Reduce Canine Infarct Size. Journal of Cardiovascular Pharmacology 16: 523-528.

Lesnefsky E J, Hoppel C L (2003) Ischemia-reperfusion injury in the aged heart: role of mitochondria. Archives of biochemistry and biophysics 420: 287-297.

Lesnefsky E J, Repine J E, Horwitz L D (1990b) Deferoxamine pretreatment reduces canine infarct size and oxidative injury. Journal of Pharmacology and Experimental Therapeutics 253: 1103-1109.

Li L, Miao R, Jia X, Ward D M, Kaplan J (2014) Expression of the yeast cation diffusion facilitators Mmt1 and Mmt2 affects mitochondrial and cellular iron homeostasis: evidence for mitochondrial iron export. The Journal of biological chemistry 289: 17132-17141.

Liang C-S, Delehanty J D (2009) Increasing Post-Myocardial Infarction Heart Failure Incidence in Elderly Patients: A Call for Action. Journal of the American College of Cardiology 53: 21-23.

Lloyd J B, Cable H, Rice-Evans C (1991) Evidence that desferrioxamine cannot enter cells by passive diffusion. Biochemical pharmacology 41: 1361-1363.

Long X, Goldenthal M J, Wu G M, Marin-Garcia J (2004) Mitochondrial $Ca^{2+}$ flux and respiratory enzyme activity decline are early events in cardiomyocyte response to $H_2O_2$. J Mol Cell Cardiol 37: 63-70.

Marcus R E, Davies S C, Bantock H M, Underwood S R, Walton S, Huehns E R (1984) Desferrioxamine to improve cardiac function in iron-overloaded patients with thalassemia major. Lancet (London, England) 1: 392-393.

McAlindon E, Bucciarelli-Ducci C, Suleiman M S, Baumbach A (2015) Infarct size reduction in acute myocardial infarction. Heart 101: 155-160.

Menasche P, Antebi H, Alcindor L G, Teiger E, Perez G, Giudicelli Y, Nordmann R, Piwnica A (1990) Iron chelation by deferoxamine inhibits lipid peroxidation during cardiopulmonary bypass in humans Circulation 82: IV390-396.

Methy D, Bertrand N, Prigent-Tessier A, Mossiat C, Stanimirovic D, Beley A, Marie C (2008) Beneficial effect of dipyridyl, a liposoluble iron chelator against focal cerebral ischemia: In vivo and in vitro evidence of protection of cerebral endothelial cells. Brain Research 1193: 136-142.

Moser M D, Matsuzaki S, Humphries K M (2009) Inhibition of succinate-linked respiration and complex II activity by hydrogen peroxide. Archives of biochemistry and biophysics 488: 69-75.

Murphy M P (2009) How mitochondria produce reactive oxygen species. The Biochemical journal 417: 1-13.

Napier I, Ponka P, Richardson D R (2005) Iron trafficking in the mitochondrion: novel pathways revealed by disease. Blood 105: 1867-1874.

Neuzil J, Widen C, Gellert N, Swettenham E, Zobalova R, Dong L F, Wang X F, Lidebjer C, Dalen H, Headrick J P et al (2007) Mitochondria transmit apoptosis signalling in cardiomyocyte-like cells and isolated hearts exposed to experimental ischemia-reperfusion injury. Redox report: communications in free radical research 12: 148-162.

Nichols M, Townsend N, Scarborough P, Rayner M, Leal J, Luengo-Fernandez R, Gray A (2012) European Cardiovascular Disease Statistics, 2012 Edition: European Heart Network, Brussels, European Society of Cardiology, Sophia Antipolis.

Nicholson S C, Squier M, Ferguson D J P, Nagy Z, Westaby S, Evans R D (1997) Effect of Desferrioxamine Cardioplegia on Ischemia-Reperfusion Injury in Isolated Rat Heart. The Annals of thoracic surgery 63: 1003-1011.

Paraskevaidis I A, Iliodromitis E K, Vlahakos D, Tsipras D P, Nikolaidis A, Marathias A, Michalis A, Kremastinos D T (2005) Deferoxamine infusion during coronary artery bypass grafting ameliorates lipid peroxidation and protects the myocardium against reperfusion injury: immediate and long-term significance. European heart journal 26: 263-270.

Pepe A, Meloni A, Capra M, Cianciulli P, Prossomariti L, Malaventura C, Putti M C, Lippi A, Romeo M A, Bisconte M G et al (2011) Deferasirox, deferiprone and desferrioxamine treatment in thalassemia major patients: cardiac iron and function comparison determined by quantitative magnetic resonance imaging. Haematologica 96:41-47.

Persson H L, Kurz T, Eaton John W, Brunk Ulf T (2005) Radiation-induced cell death: importance of lysosomal destabilization. Biochemical Journal 389: 877-884.

Petrat F, Groot Hd, Sustmann R, Rauen U (2002a) The Chelatable Iron Pool in Living Cells: A Methodically Defined Quantity. Biological Chemistry 383: 489-502.

Petrat F, Weisheit D, Lensen M, de Groot H, Sustmann R, Rauen U (2002b) Selective determination of mitochondrial chelatable iron in viable cells with a new fluorescent sensor. The Biochemical journal 362: 137-147.

Pletjushkina O Y, Lyamzaev K G, Popova E N, Nepryakhina O K, Ivanova O Y, Domnina L V, Chernyak B V, Skulachev V P (2006) Effect of oxidative stress on dynamics of mitochondrial reticulum. Biochimica et Biophysica Acta (BBA)—Bioenergetics 1757: 518-524.

Ponikowski P, van Veldhuisen D J, Comin-Colet J, Ertl G, Komajda M, Mareev V, McDonagh T, Parkhomenko A, Tavazzi L, Levesque V et al (2014) Beneficial effects of long-term intravenous iron therapy with ferric carboxymaltose in patients with symptomatic heart failure and iron deficiency. European Heart Journal 36: 657-668.

Porter J B, Wood J, Olivieri N, Vichinsky E P, Taher A, Neufeld E, Giardina P, Thompson A, Moore B, Evans P et al (2013) Treatment of heart failure in adults with thalassemia major: response in patients randomised to deferoxamine with or without deferiprone. Journal of Cardiovascular Magnetic Resonance 15:38.

Ramesh Reddy B, Kloner R A, Przyklenk K (1989) Early treatment with deferoxamine limits myocardial ischemic/reperfusion injury. Free Radical Biology and Medicine 7: 45-52.

Rauen U, Springer A, Weisheit D, Petrat F, Korth H-G, de Groot H, Sustmann R (2007) Assessment of Chelatable Mitochondrial Iron by Using Mitochondrion-Selective Fluorescent Iron Indicators with Different Iron-Binding Affinities. ChemBioChem 8: 341-352.

Roy S, Khanna S, Kuhn D E, Rink C, Williams W T, Zweier J L, Sen C K (2006) Transcriptome analysis of the ischemia-reperfused remodeling myocardium: temporal changes in inflammation and extracellular matrix. Physiological genomics 25: 364-374.

Schieber M, Chandel N S (2014) ROS function in redox signaling and oxidative stress. Current biology: CB 24: R453-462.

Shakoury-Elizeh M, Protchenko O, Berger A, Cox J, Gable K, Dunn $T_M$, Prinz W A, Bard M, Philpott C C (2010) Metabolic Response to Iron Deficiency in *Saccharomyces cerevisiae*. Journal of Biological Chemistry 285: 14823-14833.

Sideri T C, Willetts S A, Avery S V (2009) Methionine sulphoxide reductases protect iron.sulphur clusters from oxidative inactivation in yeast. Microbiology 155: 612-623.

Simoons M L, Serruys P W, van den Brand M, Res J, Verheugt F W, Krauss X H, Remme W J, Bar F, de Zwaan C, van der Laarse A et al (1986) Early thrombolysis in acute myocardial infarction: limitation of infarct size and improved survival. J Am Coll Cardiol 7: 717-728.

Spinazzi M, Casarin A, Pertegato V, Salviati L, Angelini C (2012) Assessment of mitochondrial respiratory chain enzymatic activities on tissues and cultured cells. Nature protocols 7: 1235-1246.

Steinhubl S R (2008) Why Have Antioxidants Failed in Clinical Trials? The American journal of cardiology 101: S14-S19.

Tang W H, Wu S, Wong $T_M$, Chung S K, Chung S S M (2008) Polyol pathway mediates iron-induced oxidative injury in ischemic.reperfused rat heart. Free Radical Biology and Medicine 45: 602-610.

Vasquez-Vivar J, Kalyanaraman B, Kennedy M C (2000) Mitochondrial Aconitase Is a Source of Hydroxyl Radical: an electron spin resonance investigation. Journal of Biological Chemistry 275: 14064-14069.

Verhaar M C, Westerweel P E, van Zonneveld A J, Rabelink T J (2004) Free radical production by dysfunctional eNOS. Heart 90: 494-495.

Vigani G, Tarantino D, Murgia I (2013) Mitochondrial ferritin is a functional iron-storage protein in cucumber (*Cucumis sativus*) roots. Frontiers in plant science 4: 316.

Watanabe B I, Limm W, Suehiro A, Suehiro G, Premaratne S, McNamara J J (1993) Failure of Deferoxamine to Reduce Myocardial Infarct Size in a Primate Model of Ischemia-Reperfusion Injury. Journal of Surgical Research 55: 537-542.

Williams R E, Zweier J L, Flaherty J T (1991) Treatment with deferoxamine during ischemia improves functional and metabolic recovery and reduces reperfusion-induced oxygen radical generation in rabbit hearts. Circulation 83: 1006-1014.

Wu H, Wu T, Li M, Wang J (2012) Efficacy of the lipid-soluble iron chelator 2,2 (E-dipyridyl against hemorrhagic brain injury. Neurobiology of Disease 45: 388-394.

Wu H, Xing K, Lou M F (2010) Glutaredoxin 2 prevents $H_2O_2$-induced cell apoptosis by protecting complex I activity in the mitochondria. Biochimica et Biophysica Acta (BBA)—Bioenergetics 1797: 1705-1715.

Wu R, Smeele K M, Wyatt E, Ichikawa Y, Eerbeek O, Sun L, Chawla K, Hollmann M W, Nagpal V, Heikkinen S et al (2011) Reduction in Hexokinase II Levels Results in Decreased Cardiac Function and Altered Remodeling After Ischemia/Reperfusion Injury. Circulation Research 108: 60-69.

Xu Y, Liu B, Zweier J L, He G (2008) Formation of hydrogen peroxide and reduction of peroxynitrite via dismutation of superoxide at reperfusion enhances myocardial blood flow and oxygen consumption in postischemic mouse heart. The Journal of pharmacology and experimental therapeutics 327: 402-410.

Ye H, Rouault T A (2010) Human Iron-Sulfur Cluster Assembly, Cellular Iron Homeostasis, and Disease. Biochemistry 49: 4945-4956.

Yu Z, Persson H L, Eaton J W, Brunk U T (2003) Intralysosomal iron: a major determinant of oxidant-induced cell death. Free Radical Biology and Medicine 34: 1243-1252.

Zhang X, Lemasters J J (2013) Translocation of iron from lysosomes to mitochondria during ischemia predisposes to injury after reperfusion in rat hepatocytes. Free radical biology & medicine 63: 243-253.

Zhao G, Ayene I S, Fisher A B (1997) Role of iron in ischemia-reperfusion oxidative injury of rat lungs. American Journal of Respiratory Cell and Molecular Biology 16: 293-299.

Zweier J L, Talukder M A H (2006) The role of oxidants and free radicals in reperfusion injury. Cardiovascular Research 70: 181-190.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating a subject in need thereof following cardiac ischemia, the method comprising administering to the subject a pharmaceutical composition comprising a mitochondrial permeable iron chelator, wherein the mitochondrial permeable iron chelator is 2,2'-bipyridyl.

2. The method of claim 1, wherein the method protects against ischemia/reperfusion (I/R) injury in the heart.

3. A method for treating a subject in need thereof following cardiac ischemia, the method comprising administering to the subject a pharmaceutical composition comprising a mitochondrial lipid permeable iron chelator having a logP>1, wherein the mitochondrial permeable iron chelator is a di-pyridyl compound.

4. The method of claim 3, wherein the method protects against ischemia/reperfusion (I/R) injury in the heart.

* * * * *